US012699105B2

(12) United States Patent
Xu et al.

(10) Patent No.: US 12,699,105 B2
(45) Date of Patent: Aug. 4, 2026

(54) METHODS, DEVICES, AND SYSTEMS FOR ADJUSTING LABORATORY HBA1C VALUES

(71) Applicant: ABBOTT DIABETES CARE INC., Alameda, CA (US)

(72) Inventors: Yongjin Xu, San Ramon, CA (US); Timothy C. Dunn, San Francisco, CA (US)

(73) Assignee: ABBOT DIABETES CARE INC., Alameda, CA (US)

( * ) Notice: Subject to any disclaimer, the term of this patent is extended or adjusted under 35 U.S.C. 154(b) by 811 days.

(21) Appl. No.: 17/779,370

(22) PCT Filed: Nov. 24, 2020

(86) PCT No.: PCT/US2020/062040
§ 371 (c)(1),
(2) Date: May 24, 2022

(87) PCT Pub. No.: WO2021/108419
PCT Pub. Date: Jun. 3, 2021

(65) Prior Publication Data
US 2023/0061350 A1     Mar. 2, 2023

Related U.S. Application Data

(60) Provisional application No. 63/081,599, filed on Sep. 22, 2020, provisional application No. 63/015,044, (Continued)

(51) Int. Cl.
*G01N 33/72*     (2006.01)
*A61B 5/00*     (2006.01)
(Continued)

(52) U.S. Cl.
CPC ......... *G01N 33/723* (2013.01); *A61B 5/7275* (2013.01); *G01N 33/492* (2013.01); *G16H 20/17* (2018.01); *G16H 50/20* (2018.01)

(58) Field of Classification Search
None
See application file for complete search history.

(56) References Cited

U.S. PATENT DOCUMENTS 6,175,752 B1     1/2001  Say et al.
6,421,633 B1     7/2002  Heinonen et al.
(Continued)

FOREIGN PATENT DOCUMENTS

JP          10-332704 A      12/1998
JP        2012-516735 A       7/2012
(Continued)

OTHER PUBLICATIONS

Xu et al. Correcting HbA1c Values for Individual Glycation Factors—Application of Red Blood Cell Glycation Kinetic Model. The Official Jornal Advanced Technologies & Treatments for Diabetes Conference. Feb. 20-23, 2019. 213. p. A-94 (Year: 2019).*
(Continued)

*Primary Examiner* — Adam J Eiseman
*Assistant Examiner* — Nelson Alexander Glover
(74) *Attorney, Agent, or Firm* — Workman Nydegger

(57)     ABSTRACT
Physiological parameters that related to the kinetics of red blood cell hemoglobin glycation, red blood cell elimination, and red blood cell generation within the body of a subject can be used, for example, to calculate a more reliable calculated HbA1c (cHbA1c), adjusted HbA1c (aHbA1c), and/or a personalized target glucose range, among other things, for subject-personalized diagnoses, treatments, and/or monitoring protocols. Such physiological parameters may
(Continued)

be determined using a model that considers cross-membrane glucose transport and glycation.

14 Claims, 16 Drawing Sheets

Related U.S. Application Data filed on Apr. 24, 2020, provisional application No. 62/939,970, filed on Nov. 25, 2019.

(51) Int. Cl.

| | | |
|---|---|---|
| *G01N 33/49* | (2006.01) | |
| *G16H 20/17* | (2018.01) | |
| *G16H 50/20* | (2018.01) | |

(56) References Cited

U.S. PATENT DOCUMENTS

| | | | |
|---|---|---|---|
| 2003/0212317 | A1 | 11/2003 | Kovatchev et al. |
| 2008/0009692 | A1 | 1/2008 | Stafford |
| 2011/0193704 | A1 | 8/2011 | Harper et al. |
| 2011/0213225 | A1 | 9/2011 | Bernstein et al. |
| 2011/0319729 | A1 | 12/2011 | Donnay et al. |
| 2014/0188400 | A1 | 7/2014 | Dunn et al. |
| 2014/0350369 | A1 | 11/2014 | Budiman et al. |
| 2015/0018639 | A1 | 1/2015 | Stafford |
| 2015/0025345 | A1 | 1/2015 | Funderburk et al. |
| 2015/0038816 | A1 | 2/2015 | Tokita et al. |
| 2015/0173661 | A1 | 6/2015 | Myles |
| 2018/0231573 | A1 | 8/2018 | Van et al. |
| 2018/0235524 | A1 | 8/2018 | Dunn et al. |
| 2018/0364262 | A1* | 12/2018 | Malka .................. G01N 33/723 |
| 2019/0142314 | A1 | 5/2019 | Masciotti et al. |
| 2021/0378561 | A1* | 12/2021 | Xu ........................ A61M 5/172 |
| 2023/0027904 | A1 | 1/2023 | Xu et al. |

FOREIGN PATENT DOCUMENTS

| | | | |
|---|---|---|---|
| JP | 2019-132839 | A | 8/2019 |
| WO | 2010/019372 | A1 | 2/2010 |
| WO | 2010/041439 | A1 | 4/2010 |
| WO | 2010/114929 | A1 | 10/2010 |
| WO | WO 2018/156584 | A1 | 8/2018 |
| WO | WO 2020/086934 | A2 | 4/2020 |

OTHER PUBLICATIONS

U.S. Appl. No. 62/750,957, filed Oct. 26, 2018, Xu.
U.S. Appl. No. 62/939,956, filed Nov. 25, 2019, Xu.
Bergenstal et al., "Glucose management indicator (GMI): A new term for estimating A1C from continuous glucose monitoring," Diabetes Care., 41(11): 2275-2280 (2018).
International Search Report mailed Feb. 23, 2021 corresponding to International Patent Application No. PCT/US2020/062040.
Malka et al., "Mechanistic modeling of hemoglobin glycation and red blood cell kinetics enables personalized diabetes monitoring," Sci Transl Med., 8(359), 359ra130 (2016).
Nathan et al., "Translating the A1C assay into estimated average glucose values," Diabetes Care 31(8):1473-1478 (2008) PMID: 18540046.
Xu et al., "A Kinetic Model for Glucose Levels and Hemoglobin A1c Provides a Novel Tool for Individualized Diabetes Management,", J Diabetes Sci Technol., 15(2): 294-302 (2021) DOI:10.1177/1932296819897613.
International Preliminary Report on Patentability received for PCT application No. PCT/US20/62040, mailed on Jun. 9, 2022, 11 pages.
International Preliminary Report on Patentability received for PCT application No. PCT/US20/62056, mailed on Jun. 9, 2022, 11 pages.
International search Report and written opinion received for PCT application No. PCT/US20/62056, mailed on Feb. 23, 2021, 13 pages.
Xu, Y. (2019). Correcting HBA1C Values for Individual Glycation Factors—Application of Red Blood Cell Glycation Kinetic Model Retrieved from https://dialog.proquest.com/professional/docview/2434986968?accountid=131444 (Year: 2019).
Office Action received for Canada Patent Application No. 3157577, mailed on Nov. 13, 2025, 5 pages.
Office Action received for Canada Patent Application No. 3157672, mailed on Nov. 14, 2025, 9 pages.
Office Action received for Chinese Patent Application No. 202080094338.1, mailed on Jan. 12, 2026, 10 pages.
Office Action received for Japanese Patent Application No. 2022-530750, mailed on Jan. 20, 2026, 5 pages (3 pages of English Translation and 2 pages of Original Document).
Notice of Allowance received for U.S. Appl. No. 17/779,318, mailed on Nov. 12, 2025, 9 pages.
Office Action received for Japanese Patent Application No. 2022-530750, mailed on Apr. 1, 2025, 4 pages (2 pages of English Translation and 2 pages of Original Document).
Notice of Allowance received for U.S. Appl. No. 17/779,318, mailed on Feb. 3, 2026, 2 pages.
Notice of Allowance received for U.S. Appl. No. 17/779,318, mailed on Feb. 18, 2026, 2 pages.
Office Action received for Australian Patent Application No. 2020391167, mailed on Mar. 30, 2026, 4 pages.
Office Action received for Chinese Patent Application No. 202080094338.1, mailed on Apr. 30, 2026, 6 pages.
Office Action received for European Application No. 20828883.7, mailed on May 8, 2026, 9 pages.
Office Action received for European Application No. 20828886.0, mailed on May 12, 2026, 10 pages.

* cited by examiner

Verify by matching the ending HbA1c:
Lab: 8.5%
Calculated: 8.52%

METHODS, DEVICES, AND SYSTEMS FOR ADJUSTING LABORATORY HBA1C VALUES

CROSS-REFERENCE TO RELATED APPLICATIONS

The present application is a U.S. National Stage Patent Application under 35 U.S.C. § 371 of International Patent Application No. PCT/US2020/062040, filed Nov. 24, 2020, which claims priority to US Provisional Patent Application No. 62/939,970 filed Nov. 25, 2019, US Provisional Patent Application No. 63/015,044 filed Apr. 24, 2020, and US Provisional Patent Application No. 63/081,599 filed Sep. 22, 2020, the contents of each of which are hereby incorporated herein in their entireties.

STATEMENT REGARDING FEDERALLY SPONSORED RESEARCH OR DEVELOPMENT

Not applicable.

BACKGROUND

The measurement of various analytes within an individual can sometimes be vital for monitoring the condition of their health. During normal circulation of red blood cells in a mammal such as a human body, glucose molecules attach to hemoglobin, which is referred to as glycosylated hemoglobin (also referred to as glycated hemoglobin). The higher the amount of glucose in the blood, the higher the percentage of circulating hemoglobin molecules with glucose molecules attached. Since glucose molecules stay attached to hemoglobin for the life of the red blood cells (normally about 120 days), the level of glycosylated hemoglobin reflects an average blood glucose level over that period.

Most of hemoglobin is a type called HbA. When glucose molecules attach to HbA molecules, glycosylated HbA is formed, which is referred to as HbA1. HbA1 has three components: HbA1a, HbA1b, and HbA1c. Because a glucose binds more strongly and to a higher degree to HbA1c than HbA1a and HbA1b, a measure of HbA1c in blood (HbA1c test) is often used as an indication of a subject's average blood glucose level over a 120 day period (the average lifespan of a red blood cell). The HbA1c test is performed by drawing a blood sample from a subject at a medical professional's office, which is then analyzed in a laboratory. The HbA1c test may be used as a screening and diagnostic test for pre-diabetes and diabetes. A subject's glucose exposure as determined by HbA1c levels is one of the primary factors used in making diagnosis and/or therapy decisions. That is, a normal or healthy glucose exposure is correlated to an HbA1c level or range assuming a 120 day red blood cell lifespan. A subject's laboratory HbA1c level (also referred to in the art as a measured HbA1c) is compared to this normal or health range when diagnosing and/or treating the subject.

However, while the red blood cell lifespan does not vary within a subject to a great degree (except for some subjects with specific diseases), the red blood cell lifespan for individual subjects can be between about 50 days to about 170 days. Therefore, a laboratory HbA1c level for a subject with a longer red blood cell lifespan overestimates glucose exposure and for a subject with a shorter red blood cell lifespan underestimates glucose exposure. Therefore, the diagnoses and treatments (and even if treatment should occur) are based an incorrect glucose exposure.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

Figure 1:
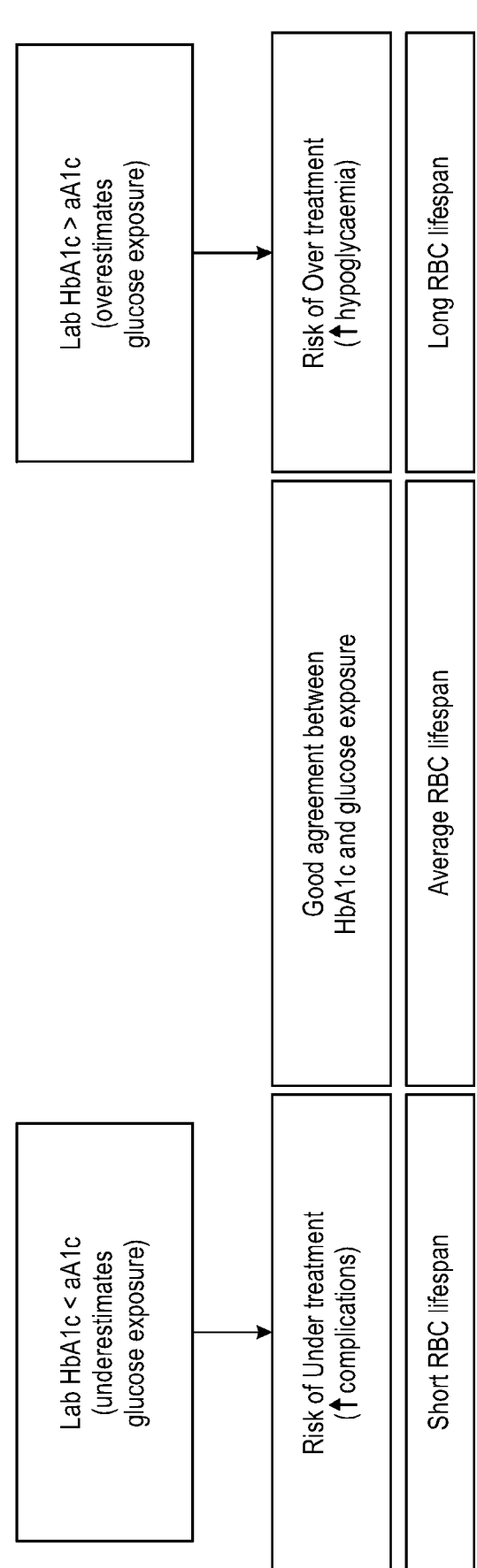
FIG. 1 illustrates that individual RBC lifespan can affect HbA1c and diabetes treatment. In this study, 31% of laboratory HbA1c can be misleading and resulting in undertreatment or overtreatment.

The present disclosure generally describes methods, devices, and systems for determining physiological parameters related to the kinetics of red blood cell glycation, elimination, and generation within the body of a subject. Such physiological parameters can be used, for example, to calculate a more reliable calculated HbA1c (cHbA1c), adjusted HbA1c (aHbA1c), and/or a personalized target glucose range, among other things, for subject-personalized diagnoses, treatments, and/or monitoring protocols.

Herein, the terms "HbA1c level," "HbA1c value," and "HbA1c" are used interchangeably. Herein, the terms "aHbA1c level," "aHbA1c value," and "aHbA1c" are used interchangeably. Herein, the terms "cHbA1c level," "cHbA1c value," and "cHbA1c" are used interchangeably.

Kinetic Model

High glucose exposure in specific organs (particularly eye, kidney and nerve) is a critical factor for the development of diabetes complications. A laboratory HbA1c (also referred to in the art as a measured HbA1c) is routinely used to assess glycemic control, but studies report a disconnect between this glycemic marker and diabetes complications in some individuals. The exact mechanisms for the failure of laboratory HbA1c to predict diabetes complications are not often clear but likely in some cases to be related to inaccurate estimation of intracellular glucose exposure in the affected organs.

Formula 1 illustrates the kinetics of red blood cell hemoglobin glycation (or referred to herein simply as red blood cell glycation), red blood cell elimination, and red blood cell generation, where "G" is free glucose, "R" is a non-glycated red blood cell, and "GR" is s glycated red blood cell hemoglobin. The rate at which glycated red blood cell hemoglobin (GR) are formed is referred to herein as a red blood cell hemoglobin glycation rate constant ($k_{gly}$, typically having units of $dL*mg^{-1}*day^{-1}$).

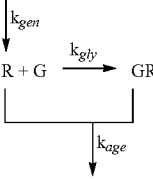

Formula 1

$$R + G \xrightarrow{k_{gly}} GR$$

Over time, red blood cell hemoglobin including the glycated red blood cell hemoglobin are continuously eliminated from a subject's circulatory system and new red blood cells containing hemoglobin are generated, typically at a rate of approximately 2 million cells per second. The rates associated with elimination and generation are referred to herein as a red blood cell elimination constant ($k_{age}$ typically having units of $day^{-1}$) and a red blood cell generation rate constant ($k_{gen}$ typically having units of $M^2$/day), respectively. Since the amount of red blood cells in the body is maintained at a stable level most of time, the ratio of $k_{age}$ and $k_{gen}$ should be an individual constant that is the square of red blood cell concentration.

Relative to glycation, Formula 2 illustrates the mechanism in more detail where glucose transporter 1 (GLUT1) facilitates glucose (G) transport into the red blood cell. Then, the intracellular glucose (GI) interacts with the hemoglobin (Hb) to produce glycated hemoglobin (HbG) where the hemoglobin glycation reaction rate constant is represented by $k_g$ (typically having units of $dL*mg^{-1}*day^{-1}$). A typical experiment measured $k_g$ value is $1.2 \times 10^{-3}$ dL/mg/day. Hemoglobin glycation reaction is a multi-step non-enzymatic chemical reaction, therefore $k_g$ should be a universal constant. The rate constant for the glucose to be transported into the red blood cell and glycated the Hb into HbG is $k_{gly}$. Then, $k_{age}$ describes red blood cell elimination (along with hemoglobin), also described herein as the red blood cell turnover rate.

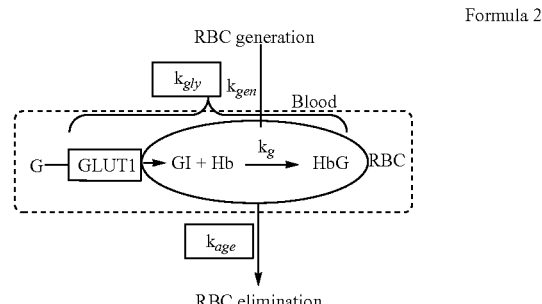

Formula 2

While raised intracellular glucose is responsible for diabetes complications, extracellular hyperglycemia selectively damages cells with limited ability to adjust cross-membrane glucose transport effectively. HbA1c has been used as a biomarker for diabetes-related intracellular hyperglycemia for two main reasons. First, the glycation reaction occurs within red blood cells (RBCs) and therefore HbA1c is modulated by intracellular glucose level. Second, RBCs do not have the capacity to adjust glucose transporter GLUT1 levels and thus are unable to modify cross-membrane glucose uptake, behaving similarly to cells that are selectively damaged by extracellular hyperglycemia. Therefore, under conditions of fixed RBC lifespan and cross-membrane glucose uptake, HbA1c mirrors intracellular glucose exposure in organs affected by diabetes complications. However, given the inter-individual variability in both cross-membrane glucose uptake and RBC lifespan, laboratory HbA1c may not always reflect intracellular glucose exposure. While variation in RBC cross-membrane glucose uptake is likely to be relevant to the risk of estimating diabetes complications in susceptible organs, red blood cell lifespan is unique to RBCs and therefore irrelevant to the complication risk in other tissues. This explains the inability to clinically rely on laboratory HbA1c in those with hematological disorders characterized by abnormal RBC turnover and represents a possible explanation for the apparent "disconnect" between laboratory HbA1c and development of complications in some individuals with diabetes (FIG. 1).

To overcome the limitations of laboratory HbA1c, a measure of personalized HbA1c has been developed, which takes into account individual variations in both RBC turnover and cellular glucose uptake. The current work aims to extend this model by adjusting for a standard RBC lifespan of 100 days (equivalent to RBC turnover rate of 1% per day, or mean RBC age of 50 days) to establish a new clinical marker, which we term adjusted HbA1c (aHbA1c). We propose that aHbA1c is the most relevant glycemic marker for estimating organ exposure to hyperglycemia and risk of future diabetes-related complications. As described previously, HbA1c is a commonly used analyte indicative of the fraction of the glycated hemoglobin found in red blood cells. Therefore, a kinetic model can be used, for example, to derive a calculated HbA1c based on at least the glucose levels measured for a subject. However, the kinetic model can also be applied to HbA1. For simplicity, HbA1c is uniformly used herein, but HbA1 could be substituted except in instances where specific HbA1c values are used. In such instances, specific HbA1 values could be used to derive similar equations.

Typically, when kinetically modeling physiological processes, assumptions are made to focus on the factors that affect the physiological process the most and simplify some of the math.

The present disclosure uses only the following set of assumptions to kinetically model the physiological process illustrated in Formulas 1 and 2. A set of assumptions were made during the model construction:

1. There is an absence of any abnormal red blood cells that would affect HbA1c measurement.
2. The glycation process has first order dependencies on concentrations of both hemoglobin in red blood cells and intracellular glucose, an assumption that is widely adopted.
3. Newly-generated red blood cells have a negligible amount of glycated hemoglobin.
4. Red blood cells are eliminated from circulation when they reach a subject specific age. The individual red blood cell elimination rate is approximated with a constant. Therefore, the glycated hemoglobin removal rate is proportional to the product of overall red blood cell elimination rate and HbA1c at the time.

With these, the rate of change in glycated and non-glycated hemoglobin in red blood cells can be modeled by differential Equations 1 and 2.

$$d[HbG]/dt = k_g[GI][Hb] - r*\alpha*A1c \qquad \text{Equation 1}$$

$$d[Hb]/dt = k_{gen}/C - r*(1 - \alpha*A1c) - k_g[GI][Hb] \qquad \text{Equation 2}$$

[HbG] and [Hb] are the concentrations of glycated and un-glycated hemoglobin, respectively, [GI] is the intracellular glucose concentration. The $k_g$ is the rate constant of hemoglobin glycation reaction in unit of $(concentration*time)^{-1}$. C is the total hemoglobin concentration where C=[Hb]+[HbG]. HbA1c is the fraction of glycated hemoglobin molecules. The r is the red blood cell removal rate in unit of concentration/time. $\alpha$ is a coefficient, which has no units of measurement, used to scale HbA1c to the fraction of glycated hemoglobin to be removed. All concentrations can take unit such as mmol/l or mg/dL. The time unit should be in hours or days.

The glucose transporter on red blood cell membranes (GLUT1) follows Michaelis-Menten kinetic. $K_M$ is the Michaelis constant that relates to the affinity of an enzyme (e.g., GLUT1) for a substrate (e.g., glucose). $K_M$ is determined experimentally. Different values for the $K_M$ for GLUT1-glucose interaction have been reported in the literature ranging from about 100 mg/dL to about 700 mg/L. Two specific example values are 306 mg/dL (17 mM) and 472 mg/dL (26.2 mM). Unless otherwise specified, $K_M$ herein is 306 mg/dL (17 mM). However, embodiments of the present disclosure are not limited to this specific $K_M$. Therefore, the intracellular glucose can be modelled with $d[GI]/dt=V_{max}*[G]/(K_M+[G])-k_c*[GI]$, where $k_c$ is the rate of glucose consumption within red blood cells. The maximum rate $V_{max}$ should be proportional to the GLUT1 level on the membrane. Both $k_c$ and $V_{max}$ can vary individually. Under equilibrium, Equation 3 is derived.

$$[GI] = \frac{V_{max}*[G]}{k_c*(K_M + [G])} = \frac{V_{max}}{K_M*k_c}g \qquad \text{Equation 3}$$

where $g=(K_M*[G])/(K_M+[G])$; $k_c$ is the rate constant for glucose consumption in the red blood cell (typically having units of $day^{-1}$); $V_{max}$ is the maximum glucose transport rate (typically having units of $mg*dL^{-1}*day^{-1}$) and should be proportional to the GLUT1 leveLI on the membrane; and $K_M$ is the Michaelis-Menten kinetic rate constant for the GLUT1 transporting glucose across the red blood cell membrane (typically having units of mM or mg/dL).

By definition, HbA1c is the fraction of the glycated hemoglobin found in red blood cells: HbA1c=[HbG]/C=(C-[Hb])/C. In steady-state, d[Hb]/dt=d[HbG]/dt=0, Equation 1 becomes C*$k_g$/($\alpha$*r)=[HbG]/([GI][Hb]). Combining with Equation 3, Equation 4 is derived.

$$\frac{C*k_g*V_{max}}{\alpha*r*K_M*k_c} = \frac{[HbG]}{g*[Hb]} \qquad \text{Equation 4}$$

By combining all parameters associated with cross-membrane glucose transport and glycation from the right-hand side of Equation 4, the composite glycation rate constant is defined as $k_{gly}=k_g*V_{max}/(k_c*K_M)$, where $k_g$ and $K_M$ are universal constants for the non-enzymatic hemoglobin glycation reaction and glucose affinity to GLUT1, respectively. Therefore, $k_{gly}$ can vary individually depending on $k_c$ and $V_{max}$. The rest of the parameters to red blood cell turnover are attributed to $k_{age}=\alpha*r/C$, which leads to the definition of apparent glycation parameter K per Equation 5.

$$K = k_{gly}/k_{age} = [HbG]/(g*[Hb]) \qquad \text{Equation 5}$$

Under a hypothetical steady-state of constant glucose level, HbA1c should reach an equilibrium level, which is the "equilibrium HbA1c" (EA). Since C=[HbG]+[Hb], Equation 5 can be re-written to K=(C-[Hb])/(g*[Hb]). Applying the definition HbA1c=(C-[Hb])/C, Equation 6 is derived.

$$EA = g/(K^{-1} + g) \qquad \text{Equation 6}$$

This relationship approximates the average glucose and HbA1c for an individual with stable day-to-day glucose profile. Equation 1 can be transformed to Equation 7.

$$d(HbA1c)/dt = k_{gly} * g * (1 - HbA1c) - r * \alpha * HbA1c/C \qquad \text{Equation 7}$$

Solving this differential equation and integrating from time 0 to t, Equation 8 is derived, for the HbA1c value HbA1c$_t$ at the end of an interval t, given a starting HbA1c (HbA1c$_0$) and assuming a constant glucose level during the time interval.

$$HbA1c_t = EA + (HbA1c_0 - EA) \cdot e^{-(k_{gly}*g + k_{age})t} \qquad \text{Equation 8}$$

To accommodate changing glucose levels over time, each subject's glucose history is approximated as a series of time intervals $t_i$ with corresponding glucose levels [G$_i$]. Applying Equation 8 recursively, HbA1c value HbA1c$_z$ (at the end of time interval $t_z$) can be expressed by Equation 9 for numerical calculations.

$$HbA1c_z = EA_z(1 - D_z) + \qquad \text{Equation 9}$$
$$\sum_{i=1}^{z-1}\left[ EA_i(1 - D_i)\prod_{j=i+1}^{z}D_j \right] + HbA1c_0\prod_{j=1}^{z}D_j$$

where $D_i = e^{-(k_{gly}*g_i + k_{age})t_i}$. The value HbA1c$_z$ is equivalent to calculated HbA1c (cHbA1c) at the end of time interval $t_z$. cHbA1c is the preferred term introduced by our work. Note that EA$_i$ and D$_i$ are both affected by k$_{gly}$, k$_{age}$ and the glucose level. In addition, D$_i$ depends on the length of the time interval $t_i$.

Equations 8 and 9 describe how HbA1c change depends on glucose level and individual kinetic constants k$_{gly}$, and k$_{age}$, which can be estimated with one or more data sections. A data section contains two HbA1c measurements, one at the start of the time period and one at the end, with frequent glucose levels in between. Also, cHbA1c can be calculated at any time given k$_{gly}$ and k$_{age}$ are available together with an earlier HbA1c and frequent glucose measurements. The purpose of the frequent glucose measurements is to calculate average glucose ([G$_i$]) in pre-defined time intervals (t$_i$). In this study, frequent glucose levels were measured in the interval of 15 minutes, and time intervals (t$_i$) examined were of 3 hours, 6 hours, 12 hours, 24 hours, and 36 hours. Calculating Physiological Parameters from the Kinetic Model Embodiments of the present disclosure provide kinetic modeling of red blood cell glycation, elimination, and generation within the body of a subject.

The physiological parameters k$_{gly}$, k$_{age}$, and/or K can be derived from the equations described herein given at least one laboratory HbA1c value (also referred to as HbA1c level measurement) and a plurality of glucose levels (also referred to as glucose level measurements) over a time period immediately before the HbA1c measurement.

Figure 2:
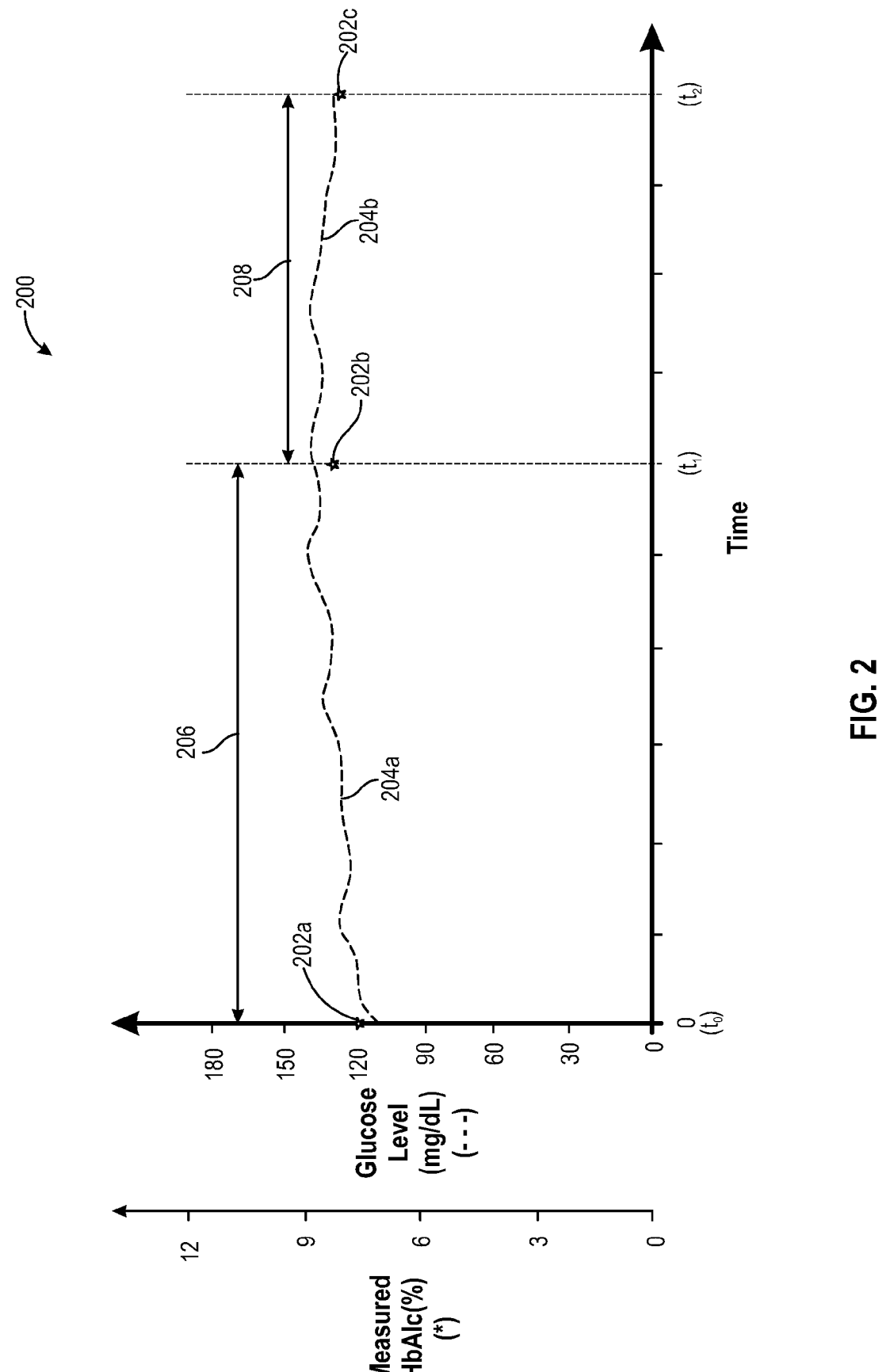
FIG. 2 illustrates an example time line illustrating collection of at least one HbA1c value and a plurality of glucose levels for a time period.

FIG. 2 illustrates an example time line 200 illustrating collection of at least one laboratory HbA1c value 202a, 202b, 202c and a plurality of glucose levels 204a for a time period 206.

The number of laboratory HbA1c values 202a, 202b, 202c needed to calculate k$_{gly}$, k$_{age}$, and/or K depends on the frequency and duration of the plurality of glucose levels, and the dynamics over time of the HbA1c values and glucose levels.

In a first embodiment, one laboratory HbA1c 202b can be used along with a plurality of glucose measurements over time period 206 to calculate k$_{gly}$, k$_{age}$, and/or K. Such embodiments are applicable to subjects with steady daily glucose measurements for a long time period 206.

k$_{gly}$ and k$_{age}$ may be calculated with Equation 9 when the glucose levels are measured for a sufficient amount of time (e.g., over about 200 days) because $$HbA1c_0\prod_{j=1}^{z}D_j$$

approaches zero when the time is long. Therefore, an initial HbA1c level measurement is not necessarily required.

Because a first HbA1c value is not measured, the time period 206 of initial glucose level measurements with frequent measurements may need to be long to obtain an accurate representation of average glucose and reduce error. Using more than 100 days of steady glucose pattern for this method may reduce error. Additional length like 200 days or more or 300 days or more further reduces error.

Embodiments where one laboratory HbA1c value 202b can be used include a time period 206 about 100 days to about 300 days (or longer) with glucose levels being measured at least about 72 times (e.g., about every 20 minutes) to about 96 times per day (e.g., about every 15 minutes) or more often. Further, in such embodiments, the time between glucose level measurements may be somewhat consistent where an interval between two glucose level measurements should not be more than about an hour. Some missing data glucose measurements are tolerable when using only one laboratory HbA1c value. Increases in missing data may lead to more error.

Alternatively, in some instances where one laboratory HbA1c value 202b is used, the time period 206 may be shortened if a subject has an existing glucose level monitoring history with stable, consistent glucose profile. For example, for a subject who has been testing for a prolonged time (e.g., 6 months or longer) but, perhaps, at less frequent or regimented times, the existing glucose level measurements can be used to determine and analyze a glucose profile. Then, if more frequent and regimented glucose monitoring is performed over time period 206 (e.g., about 72 times to about 96 times or more per day over about 14 days or more) followed by measurement of HbA1c 202b, the three in combination may be used to calculate one or more physiological parameters (k$_{gly}$, k$_{age}$, and/or K) at time t$_1$.

Alternatively, in some embodiments, two laboratory HbA1c values may be used with a first laboratory HbA1c value 202a at the beginning of a time period 206, a second laboratory HbA1c value 202b at the end of the time period 206, and a plurality of glucose levels 204a measured during the time period 206. In these embodiments, Equation 9 may be used to calculate one or more physiological parameters (k$_{gly}$, k$_{age}$, and/or K) at time t$_1$. In such embodiments, the plurality of glucose levels 204a may be measured for about 10 days to about 30 days or longer with measurements being, on average, about 4 times daily (e.g., about every 6 hours) to about 24 times daily (e.g., about every 1 hour) or more often.

The foregoing embodiments are not limited to the example glucose level measurement time period and frequency ranges provided. Glucose levels may be measured over a time period of about a few days to about 300 days or more (e.g., about one week or more, about 10 days or more, about 14 days or more, about 30 days or more, about 60 days or more, about 90 days or more, about 120 days or more, and so on). The frequency of such glucose levels may be, on average, about 14,400 times daily (e.g., about every 10 seconds) (or more often) to about 3 times daily (e.g., about every 8 hours) (e.g., 1,440 times daily (e.g., about every minute), about 288 times daily (e.g., about every 5 minutes), about 144 times daily (e.g., about every 10 minutes), about 96 times daily (e.g., about every 15 minutes), about 72 times daily (e.g., about every 20 minutes), about 48 times daily (e.g., about every 30 minutes), about 24 times daily (e.g., about every 1 hour), about 12 times daily (e.g., about every 2 hours), about 8 times daily (e.g., about every 3 hours), about 6 times daily (e.g., about every 4 hours), about 4 times daily (e.g., about every 6 hours), and so on). In some instances, less frequent monitoring (like once or twice daily) may be used where the glucose measurements occur at about the same time (within about 30 minutes) daily to have a more direct comparison of day-to-day glucose levels and reduce error in subsequent analyses.

The foregoing embodiments may further include calculating an error or uncertainty associated with the one or more physiological parameters. In some embodiments, the error may be used to determine if another HbA1c value (not illustrated) should be measured near $t_1$, if one or more glucose levels 204$b$ should be measured (e.g., near $t_1$), if the monitoring and analysis should be extended (e.g., to extend through time period 208 from $t_1$ to $t_2$ including measurement of glucose levels 204$b$ and measurement HbA1c value 202$c$ at time $t_2$), and/or if the frequency of glucose level measurements 204$b$ in an extended time period 208 should be increased relative to the frequency of glucose level measurements 204$a$ during time period 206. In some embodiments, one or more of the foregoing actions may be taken when the error (e.g., error from the HbA1c assay) associated with $k_{gly}$, $k_{age}$, and/or K is at or greater than about 15%, preferably at or greater than about 10%, preferably at or greater than about 7%, and preferably at or greater than about 5%. When a subject has an existing disease condition (e.g., cardiovascular disease), a lower error may be preferred to have more stringent monitoring and less error in the analyses described herein.

Alternatively or when the error is acceptable, in some embodiments, one or more physiological parameters ($k_{gly}$, $k_{age}$, and/or K) at time $t_1$ may be used to determine one or more parameters or characteristics for a subject's personalized diabetes management (e.g., a cHbA1c at the end of time period 208, a personalized-target glucose range, and/or a treatment or change in treatment for the subject in the near future), each described in more detail further herein. Optionally, a HbA1c value may be measured at time $t_2$ and the one or more physiological parameters recalculated and applied to a future time period (not illustrated).

The one or more physiological parameter and/or the one or more parameters or characteristics for a subject's personalized diabetes management can be measured and/or calculated for two or more times (e.g., $t_1$ and $t_2$) and compared. For example, $k_{gly}$ at $t_1$ and $t_2$ may be compared. In another example, cHbA1c at $t_2$ and at a future time may be compared. Some embodiments, described further herein, may use such comparisons to (1) monitor progress and/or effectiveness of a subject's personalized diabetes management and, optionally, alter the subject's personalized diabetes management, (2) identify an abnormal or diseased physiological condition, and/or (3) identify subjects taking supplements and/or medicines that effect red blood cell production and/or effect metabolism.

In each of the example methods, devices, and systems utilizing the one or more physiological parameters ($k_{gly}$, $k_{age}$, and K) and related analyses (e.g., personalized-target glucose range, personalized-target average glucose, cHbA1c, aHbA1c, and the like). The one or more physiological parameters ($k_{gly}$, $k_{age}$, and K) and related analyses may be updated periodically (e.g., about every 3 months to annually). The frequency of updates may depend on, among other things, the subject's glucose level and diabetes history (e.g., how well the subject stays within the prescribed thresholds), other medical conditions, and the like.

Adjusted HbA1c

In the diabetes and red blood cell glycation arts, the generally accepted average RBC lifespan may change. While the reference RBC lifespan may be outside these ranges, the $k^{ref}_{age}$ preferably reflects a reference average RBC lifespan of 85 days to 135 days, or 85 days to 110 days, or 90 days to 110 days, or 95 days to 125 days, or 110 days to 135 days. Most preferably, the $k^{ref}_{age}$ reflects a reference RBC lifespan of 85 days to 110 days, or 90 days to 110 days, or 100 days. Herein, $k^{ref}_{age}$ equals 0.01 day$^{-1}$ for all examples. However, embodiments of the present disclosure are not limited to this specific $k^{ref}_{age}$.

The aHbA1c for a subject can be calculated via Equation 10 using the HbA1c level for said subject, the $k_{age}$ for said subject, and the $k^{ref}_{age}$.

$$aHbA1c = \frac{HbA1c}{HbA1c + \frac{k^{ref}_{age}}{k_{age}}(1 - HbA1c)} \qquad \text{Equation 10}$$

where HbA1c may be cHbA1c described herein or a laboratory HbA1c.

Usually, $K = k_{gly}/k_{age}$ requires only one data section to determine in high confidence. Since a larger K value usually correlates with smaller $k_{age}$ values, it is possible to generate an approximate aHbA1c with K in the early stage of data acquisition when $k_{age}$ is not yet available (Equation 11). A typical $K^{ref}$ value is, for example, $5.2 \times 10^{-4}$ dL/mg. However, embodiments of the present disclosure are not limited to this specific $K^{ref}$.

$$aHbA1c = \frac{HbA1c}{HbA1c + \frac{K}{K^{ref}}(1 - HbA1c)} \qquad \text{Equation 11}$$

where HbA1c may be cHbA1c described herein or a laboratory HbA1c.

The aHbA1c for a subject (based, at least in part, on a laboratory HbA1c and/or a calculated HbA1c) can then be used for diagnoses, treatments, and/or monitoring protocols of said subject. For example, the subject may be diagnosed with diabetes, pre-diabetes, or another abnormal or diseased physiological condition based, at least in part, on the aHbA1c described herein. In another example, the subject may be monitored and/or treated with insulin self-monitoring and/or injections, continuous insulin monitoring and/or injections, and the like based, at least in part, on the aHbA1c described herein. In yet another example, the aHbA1c described herein may be used for determining and/or administering a personalized treatment for subject triage, determining and/or administering a personalized treatment for titration of diabetes medication, determining and/or administering a personalized closed-loop or hybrid-closed loop control system, determining and/or administering a personalized treatment using glycation medications, determining of physiological age, identifying if and/or what supplements and/or medicines are present during testing, and the like, and any combination thereof.

By removing the interference from RBC turnover rate variation, aHbA1c is a better individual biomarker than HbA1c for the risk of complications in people with diabetes. The aHbA1c can be higher and lower than laboratory HbA1c and which will make significant differences in diabetes diagnosis and management. For an individual with faster than usual RBC turnover rate, a typical observation in patients with kidney disease or after heart valve surgery, HbA1c is artificially low and give people illusion of good glycemic control. In contrary, slower than normal RBC turnover will lead to artificially high HbA1c and lead to over-zealous treatment and may cause dangerous hypoglycemia.

In an example, a $k_{age}$ of 0.0125 day$^{-1}$ (or RBC lifespan of 80 days) and laboratory HbA1c 7% would lead to aHbA1c of 8.6%. A laboratory HbA1c of 7% without adjustment for RBC turnover rate indicates good glycemic control. However, said HbA1c value is an underestimate, where the more accurate value adjusted for RBC turnover rate (aHbA1c) of 8.6%, which indicates a higher complication risk for said subject.

In another example, a $k_{age}$ of 0.0077 day$^{-1}$ (or RBC lifespan of 130 days) and a seemingly high laboratory HbA1c 9% would lead to aHbA1c of 7.1%. The seemingly high laboratory HbA1c of 9% would indicate a poor glycemic control and significant complication risk. However the person has low complication risk by aHbA1c of 7.1%. Working from the laboratory HbA1c value of 9%, said subject would likely receive treatment that could the subject at risk for hypoglycemia because the aHbA1c is 7.1%.

When only K is available, aHbA1c can be estimated with Equation 11. For example, when the laboratory HbA1c is 8% and a high K value of $6 \times 10^{-4}$ day$^{-1}$ is determined, an aHbA1c estimation of 7%. This adjustment is usually conservative and, therefore, safe to use when $k_{age}$ is not yet available. In this example, unnecessary, and potentially harmful, treatment may be given based on the laboratory HbA1c value when no treatment should be given based on the aHbA1c value.

In another example, when the laboratory HbA1c is 7% and a low K value of $4 \times 10^{-4}$ day$^{-1}$ is determined, the estimated aHbA1c is 8.9%. In this instance, treatment may not be given when relying solely on the laboratory HbA1c value but should be given because of the high aHbA1c.

The $k^{ref}_{age}$ herein is a predetermined value used as a reference average RBC turnover rate that describes the RBC lifespan. A RBC turnover rate is 1 divided by the RBC lifespan*100 (or $k_{age}$=(1/RBC lifespan)*100) to give $k_{age}$ the units of 1% per day. $k^{ref}_{age}$ is calculated the same way using the desired reference average RBC lifespan.

The $k_{age}$ of a subject can be determined by a variety of methods including, but not limited to, methods described in herein; in US Pat. App. Pub. No. 2018/0235524; in U.S. Prov. Pat. App. No. 62/750,957; and in U.S. Prov. Pat. App. No. 62/939,956; each of which is incorporated herein by reference in their entirety for all purposes.

The HbA1c may be measured in a laboratory and/or calculated (e.g., as described herein as cHbA1c) based, at least in part, on glucose monitoring data. Preferably, said glucose monitoring data is continuous with little to no missed readings to provide higher accuracy in the calculated HbA1c level. Herein, when an HbA1c is described as calculated, the HbA1c level may be referred to in the art as calculated or estimated. Several methods can be used for calculating (or estimating) an HbA1c level including, but not limited to, the eAG/A1C Conversion Calculator provided by the American Diabetes Association; glucose management indicator (GMI) methods (e.g., methods described in *Glucose management indicator (GMI): A new term for estimating A1C from continuous glucose monitoring Diabetes* 41(11): 2275-2280 November 2018); methods described in *Translating the A1C assay into estimated average glucose values* Diabetes Care 31(8):1473-8 Aug. 2008 PMID: 18540046; methods described in *Mechanistic modeling of hemoglobin glycation and red blood cell kinetics enables personalized diabetes monitoring* Sci. Transl. Med. 8, 359ra130 October 2016; US Pat. App. Pub. No. 2018/0235524; U.S. Prov. Pat. App. No. 62/750,957; and U.S. Prov. Pat. App. No. 62/939,956; and the like; and any hybrid thereof. Each of the foregoing patent applications are incorporated herein by reference in their entirety for all purposes.

Methods of the present disclosure include determining (e.g., measuring and/or calculating based on glucose monitoring) a HbA1c level for a subject; determining a RBC elimination rate constant (also referred to as RBC turnover rate and $k_{age}$, typically having units of day$^{-1}$) for the subject; and calculating an adjusted HbA1c value (aHbA1c) for the subject based on the HbA1c level, the $k_{age}$, and a defined reference $k_{age}$ ($k^{ref}_{age}$). Then, the subject may be diagnosed, treated, and/or monitored based on the aHbA1c.

A nonlimiting example method of the present disclosure may comprise: providing (or taking) a plurality of blood glucose measurements for the subject; calculating a HbA1c for the subject based, at least in part, on the plurality of blood glucose measurements; providing (or determining) a $k_{age}$ for a subject; and calculating an aHbA1c for the subject based on the HbA1c level, the $k_{age}$, and a $k^{ref}_{age}$. Then, the subject may be diagnosed, treated, and/or monitored based on the aHbA1c.

Another nonlimiting example method of the present disclosure may comprise: providing (or measuring) a HbA1c for a subject based; providing (or determining) a $k_{age}$ for a subject; and calculating an aHbA1c for the subject based on the HbA1c level, the $k_{age}$, and a $k^{ref}_{age}$. Then, the subject may be diagnosed, treated, and/or monitored based on the aHbA1c.

Other Factors

In some of the embodiments described herein that apply the one or more physiological parameters ($k_{gly}$, $k_{age}$, and/or K), one or more other subject-specific parameters may be used in addition to the one or more physiological parameters. Examples of subject-specific parameters may include, but are not limited to, an existing medical condition (e.g., cardiovascular disease, heart valve replacement, cancer, and systemic disorder such as autoimmune disease, hormone disorders, and blood cell disorders), a family history of a medical condition, a current treatment, an age, a race, a gender, a geographic location (e.g., where a subject grew up or where a subject currently lives), a diabetes type, a duration of diabetes diagnosis, and the like, and any combination thereof.

Systems

In some embodiments, determining the one or more physiological parameters ($k_{gly}$, $k_{age}$, and/or K) for a subject may be performed using a physiological parameter analysis system.

Figure 3:
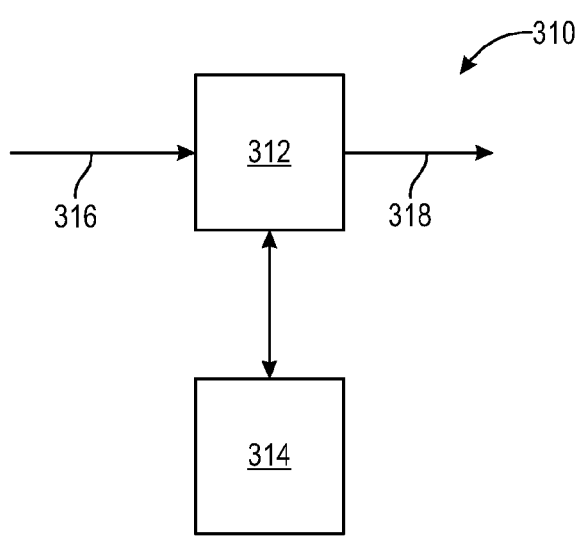
FIG. 3 illustrates an example of a physiological parameter analysis system for providing physiological parameter analysis in accordance with some of the embodiments of the present disclosure.

FIG. 3 illustrates an example of a physiological parameter analysis system 310 for providing physiological parameter analysis in accordance with some of the embodiments of the present disclosure. The physiological parameter analysis system 310 includes one or more processors 312 and one or more machine-readable storage media 314. The one or more machine-readable storage media 314 contains a set of instructions for performing a physiological parameter analysis routine, which are executed by the one or more processors 312.

In some embodiments, the instructions include receiving inputs 316 (e.g., one or more glucose levels, one or more HbA1c levels, one or more physiological parameters ($k_{gly}$, $k_{age}$, and/or K) previously determined, or more other subject-specific parameters, and/or one or more times associated with any of the foregoing), determining outputs 318 (e.g., one or more physiological parameters ($k_{gly}$, $k_{age}$, and/or K), an error associated with the one or more physiological parameters, one or more parameters or characteristics for a subject's personalized diabetes management (e.g., cHbA1c, aHbA1c, a personalized-target glucose range, an average-target glucose level, a supplement or medication dosage, among other parameters or characteristics), and the like), and communicating the outputs 318. In some embodiments, communication of the inputs 316 may be via a user-interface (which may be part of a display), a data network, a server/cloud, another device, a computer, or any combination thereof, for example. In some embodiments, communication of the outputs 318 may be to a display (which may be part of a user-interface), a data network, a server/cloud, another device, a computer, or any combination thereof, for example.

A "machine-readable medium", as the term is used herein, includes any mechanism that can store information in a form accessible by a machine (a machine may be, for example, a computer, network device, cellular phone, personal digital assistant (PDA), manufacturing tool, any device with one or more processors, and the like). For example, a machine-accessible medium includes recordable/non-recordable media (e.g., read-only memory (ROM), random access memory (RAM), magnetic disk storage media, optical storage media, flash memory devices, and the like).

In some instances, the one or more processors 312 and the one or more machine-readable storage media 314 may be in a single device (e.g., a computer, network device, cellular phone, PDA, an analyte monitor, and the like).

Figure 4:
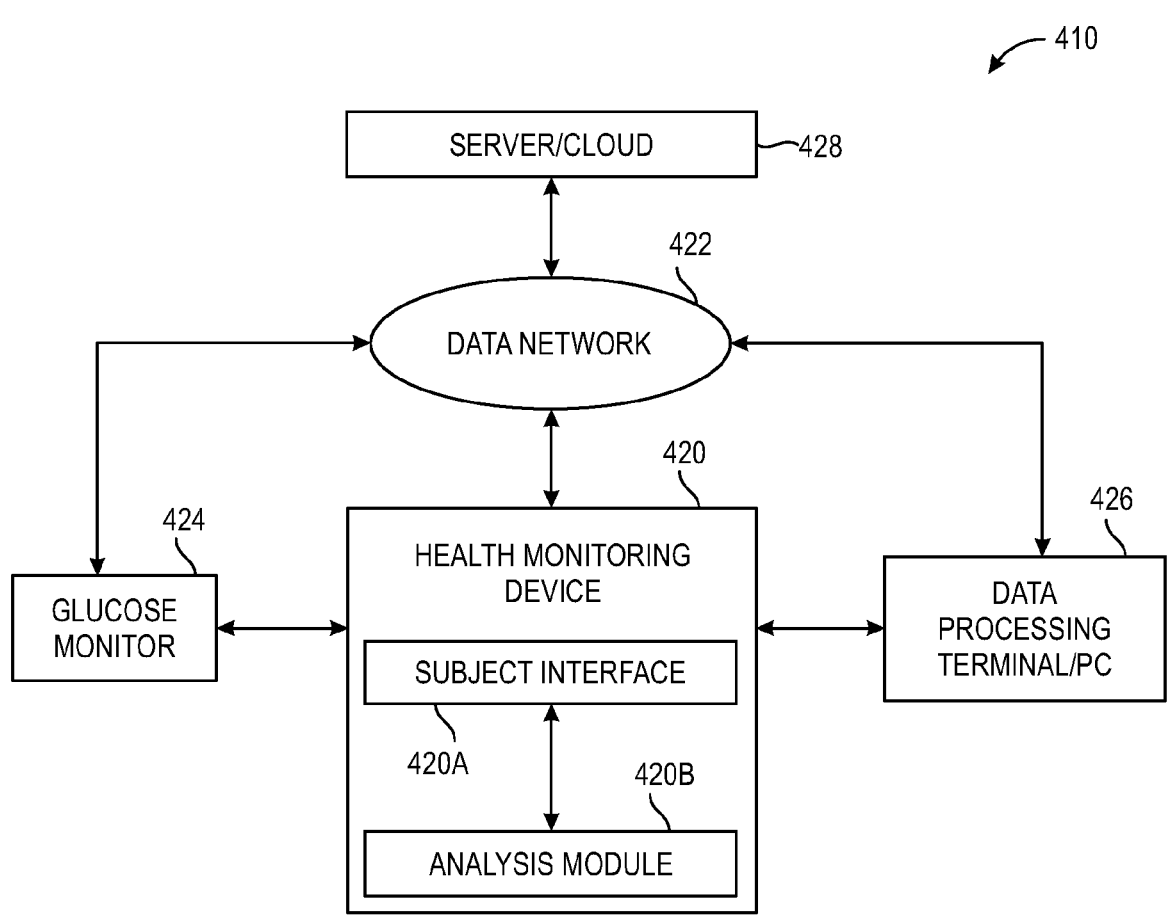
FIG. 4 illustrates an example of a physiological parameter analysis system for providing physiological parameter analysis in accordance with some of the embodiments of the present disclosure.

In some embodiments, a physiological parameter analysis system may include other components. FIG. 4 illustrates another example of a physiological parameter analysis system 410 for providing physiological parameter analysis in accordance with some of the embodiments of the present disclosure.

The physiological parameter analysis system 410 includes health monitoring device 420 with subject interface 420A and analysis module 420B, the health monitoring device 420 is, or may be, operatively coupled to data network 422. Also provided in physiological parameter analysis system 410 is a glucose monitor 424 (e.g., in vivo and/or in vitro (ex vivo) devices or system) and a data processing terminal/personal computer (PC) 426, each operatively coupled to health monitoring device 420 and/or data network 422. Further shown in FIG. 4 is server/cloud 428 operatively coupled to data network 422 for bi-directional data communication with one or more of health monitoring device 420, data processing terminal/PC 426 and glucose monitor 424. Physiological parameter analysis system 410 within the scope of the present disclosure can exclude one or more of server/cloud 428, data processing terminal/PC 426 and/or data network 422.

In certain embodiments, analysis module 420B is programmed or configured to perform physiological parameter analysis and, optionally, other analyses (e.g., cHbA1c, aHbA1c, personalized target glucose range, and others described herein). As illustrated, analysis module 420B is a portion of the health monitoring device 420 (e.g., executed by a processor therein). However, the analysis module 420B may alternatively be associated with one or more of server/cloud 428, glucose monitor 424, and/or data processing terminal/PC 426. For example, one or more of server/cloud 428, glucose monitor 424, and/or data processing terminal/PC 426 may comprise machine-readable storage medium (media) with a set of instructions that cause one or more processors to execute the set of instructions corresponding to the analysis module 420B.

While the health monitoring device 420, the data processing terminal/PC 426, and the glucose monitor 424 are illustrated as each operatively coupled to the data network 422 for communication to/from the server/cloud 428, one or more of the health monitoring device 420, the data processing terminal/PC 426, and the glucose monitor 424 can be programmed or configured to directly communicate with the server/cloud 428, bypassing the data network 422. The mode of communication between the health monitoring device 420, the data processing terminal/PC 426, and the glucose monitor 424 and the data network 422 includes one or more wireless communication, wired communication, RF communication, BLUETOOTH® communication, WiFi data communication, radio frequency identification (RFID) enabled communication, ZIGBEE® communication, or any other suitable data communication protocol, and that optionally supports data encryption/decryption, data compression, data decompression and the like.

As described in further detail below, the physiological parameter analysis can be performed by one or more of the health monitoring device 420, data processing terminal/PC 426, glucose monitor 424, and server/cloud 428, with the resulting analysis output shared in the physiological parameter analysis system 410.

Additionally, while the glucose monitor 424, the health monitoring device 420, and the data processing terminal/PC 426 are illustrated as each operatively coupled to each other via communication links, they can be modules within one integrated device (e.g., sensor with a processor and communication interface for transmitting/receiving and processing data).

Measuring Glucose and HbA1c Levels

The measurement of the plurality of glucose levels through the various time periods described herein may be done with in vivo and/or in vitro (ex vivo) methods, devices, or systems for measuring at least one analyte, such as glucose, in a bodily fluid such as in blood, interstitial fluid (ISF), subcutaneous fluid, dermal fluid, sweat, tears, saliva, or other biological fluid. In some instances, in vivo and in vitro methods, devices, or systems may be used in combination.

Examples of in vivo methods, devices, or systems measure glucose levels and optionally other analytes in blood or ISF where at least a portion of a sensor and/or sensor control device is, or can be, positioned in a subject's body (e.g., below a skin surface of a subject). Examples of devices include, but are not limited to, continuous analyte monitoring devices and flash analyte monitoring devices. Specific devices or systems are described further herein and can be found in U.S. Pat. No. 6,175,752 and US Patent Application Publication No. 2011/0213225, the entire disclosures of each of which are incorporated herein by reference for all purposes In vitro methods, devices, or systems (including those that are entirely non-invasive) include sensors that contact the bodily fluid outside the body for measuring glucose levels. For example, an in vitro system may use a meter device that has a port for receiving an analyte test strip carrying bodily fluid of the subject, which can be analyzed to determine the subject's glucose level in the bodily fluid. Additional devices and systems are described further below.

As described above the frequency and duration of measuring the glucose levels may vary from, on average, about 3 times daily (e.g., about every 8 hours) to about 14,400 times daily (e.g., about every 10 seconds) (or more often) and from about a few days to over about 300 days, respectively.

Once glucose levels are measured, the glucose levels may be used to determine the one or more physiological parameters ($k_{gly}$, $k_{age}$, and/or K) and, optionally, other analyses (e.g., cHbA1c, aHbA1c, personalized target glucose range, and others described herein). In some instance, such analyses may be performed with a physiological parameter analysis system. For example, referring back to FIG. 4, in some embodiments, the glucose monitor 424 may comprise a glucose sensor coupled to electronics for (1) processing signals from the glucose sensor and (2) communicating the processed glucose signals to one or more of health monitoring device 420, server/cloud 428, and data processing terminal/PC 426.

The measurement of one or more HbA1c levels at the various times described herein may be according to any suitable method. Typically, HbA1c levels are measured in a laboratory using a blood sample from a subject. Examples of laboratory tests include, but are not limited to, a chromatography-based assay, an antibody-based immunoassay, and an enzyme-based immunoassay. HbA1c levels may also be measured using electrochemical biosensors.

The frequency of HbA1c level measurements may vary from, on average, monthly to annually (or less often if the average glucose level of the subject is stable).

Once glucose levels are measured, the glucose levels may be used to determine the one or more physiological parameters and, optionally, other analyses described herein. In some instance, such analyses may be performed with a physiological parameter analysis system. For example, referring back to FIG. 4, in some embodiments, HbA1c levels may be measured with a laboratory test where the results are input to the server/cloud 428, the subject interface 420A, and/or a display from the testing entity, a medical professional, the subject, or other user. Then, the HbA1c levels may be received by the one or more of health monitoring device 420, server/cloud 428, and data processing terminal/PC 426 for analysis by one or more methods described herein.

Calculated HbA1c (cHbA1c)

After one or more physiological parameters ($k_{gly}$, $k_{age}$, and/or K) are calculated, a plurality of glucose measurements may be taken for a following time period and used for calculating HbA1c during and/or at the end of the following time period. For example, referring back to FIG. 2, one or more physiological parameters ($k_{gly}$, $k_{age}$, and/or K) may be calculated at time $t_1$ based on measurements of the plurality of glucose levels 204a over time period 206, a laboratory HbA1c level 202b at the end of time period 206, and optionally a laboratory HbA1c level 202a at the beginning of time period 206. Then, for a subsequent time period 208, a plurality of glucose levels 204b may be measured. Then, during and/or at the end of the time period 204b, Equation 9 can be used to determine a cHbA1c value (HbA1c$_z$ of Equation 9) where HbA1c$_0$ is the laboratory HbA1c level 202b at the end of time period 206 (which is the beginning of time period 208), [G$_i$] are the glucose levels or averaged glucose levels at times $t_i$ measured over time period 208 (or the portion of time period 208 where cHbA1c is determined during the time period 208), and the provided one or more physiological parameters ($k_{gly}$, $k_{age}$, and/or K) corresponding to time $t_1$ are used.

A subject's cHbA1c may be determined for several successive time periods based on the one or more physiological parameters ($k_{gly}$, $k_{age}$, and/or K) determined with the most recent laboratory HbA1c level and the intervening measurements of glucose levels. The HbA1c may be measured periodically (e.g., every 6 months to a year) to recalculate the one or more physiological parameters. The time between evaluating a laboratory HbA1c may depend on (1) the consistency of the measurements of glucose levels, (2) the frequency of the measurements of glucose levels, (3) a subject's and corresponding family's diabetic history, (4) the length of time the subject has been diagnosed with diabetes, (5) changes to a subject's personalized diabetes management (e.g., changes in medications/dosages, changes in diet, changes in exercise, and the like), and combinations thereof. For example, a subject with consistent measurements of glucose levels (e.g., a [G] with less than 5% variation) and frequent measurements of glucose levels (e.g., continuous glucose monitoring) may measure HbA1c levels less frequently than a subject who recently (e.g., within the last 6 months) changed the dosage of a glycation medication even with consistent and frequent measurements of glucose levels.

Figure 5:
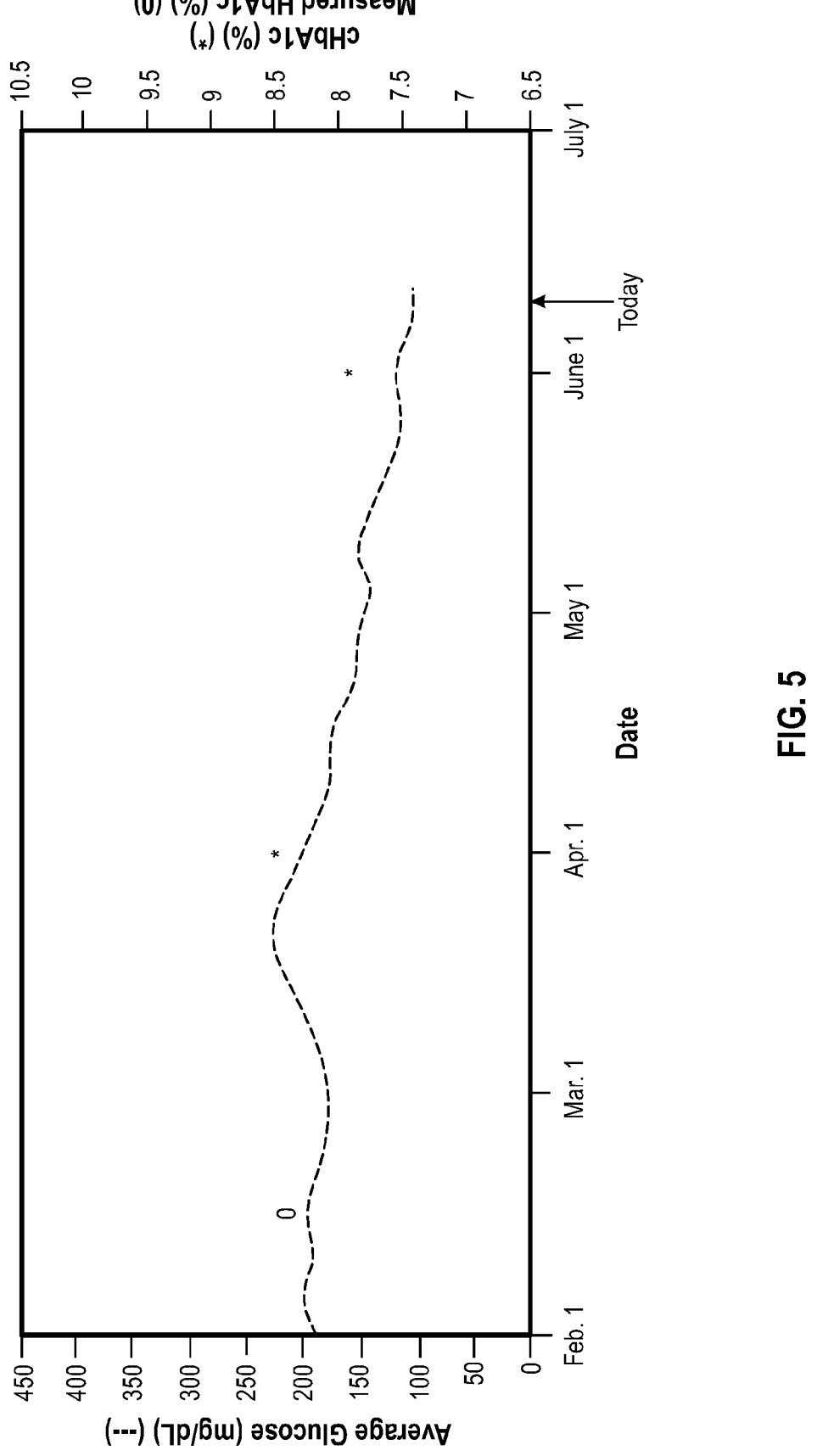
FIG. 5 illustrates an example of a cHbA1c report that may be generated as an output by a physiological parameter analysis system in accordance with some of the embodiments of the present disclosure.

FIG. 5, with reference to FIG. 3, illustrates an example of a cHbA1c report that may be generated as an output 318 by a physiological parameter analysis system 310 of the present disclosure. The illustrated example report includes a plot of average glucose level over time. Also included on the report is the most recently laboratory HbA1c level (open circle) and cHbA1c levels (asterisks) calculated by the physiological parameter analysis system 310. Two cHbA1c levels are illustrated, but one or more cHbA1c levels may be displayed on the report, including a line that continuously tracks cHbA1c. Alternatively, the output 318 of the physiological parameter analysis system 310 may include a single number for a current or most recently calculated cHbA1c, aHbA1c, a table corresponding to the data of FIG. 5, or any other report that provides a subject, healthcare provider, or the like with at least one cHbA1c level.

In some instances, the cHbA1c may be compared to a previous cHbA1c and/or a previous laboratory HbA1c level to monitor the efficacy of a subject's personalized diabetes management. For example, if a diet and/or exercise plan is being implemented as part of a subject's personalized diabetes management, with all other factors (e.g., medication and other diseases) equal, then changes in the cHbA1c compared to the previous cHbA1c and/or the previous laboratory HbA1c level may indicate if the diet and/or exercise plan is effective, ineffective, or a gradation therebetween.

In some instances, the cHbA1c may be compared to a previous cHbA1c and/or a previous laboratory HbA1c level to determine if another HbA1c measurement should be taken. For example, in absence of significant glucose profile change, if the cHbA1c changes by 0.5 percentage units or more (e.g., changes from 7.0% to 6.5% or from 7.5% to 6.8%) as compared to the previous cHbA1c and/or the previous laboratory HbA1c level, another laboratory HbA1c level may be tested.

In some instances, a comparison of the cHbA1c to a previous cHbA1c and/or a previous laboratory HbA1c level may indicate if an abnormal or diseased physiological condition is present. For example, if a subject has maintained a cHbA1c and/or laboratory HbA1c level for an extended period of time, then if a change in cHbA1c is identified with no other obvious causes, the subject may have a new abnormal or diseased physiological condition. Indications of what that new abnormal or diseased physiological condition may be gleaned from the one or more physiological parameters ($k_{gly}$, $k_{age}$, and/or K). Details of abnormal or diseased physiological conditions relative to the one or more physiological parameters are discussed further herein.

Personalized-Target Glucose Range and Personalized Glucose Level

Typically, the glucose levels in subjects with diabetes is preferably maintained between 70 mg/dL and 180 mg/dL. However, the kinetic model described herein illustrates that the intracellular glucose levels are dependent on physiological parameters like $k_{gly}$. Further, the intracellular glucose level is associated with hypoglycemia and hyperglycemia damage to organs, tissues, and cells. Therefore, a measured glucose level may not actually correspond to the actual physiological conditions that relevant to diabetes management in a subject. For example, a subject with a higher than normal $k_{gly}$ uptakes glucose more readily into cells. Therefore, a 180 mg/dL measured glucose level may be too high for the subject and, in the long run, further continue the subject's diabetes. In another example, a subject with a lower than normal $k_{gly}$ uptakes glucose to a lesser degree into cells. Accordingly, at a 70 mg/dL glucose level, the subject's intracellular glucose level may be much lower making the subject feel weak and, in the long term, lead to the subject being hypoglycemic.

Herein, three methods are presented for taking into account a subject's specific $k_{gly}$ with respect to a glucose reading and/or a corresponding personalized glucose range: (a) adjusting the accepted normal glucose upper and lower limits to arrive at a personalized-target glucose range that is based on $k_{gly}$, (b) adjusting a subject's measured glucose level to an effective plasma glucose level that correlates to the accepted normal glucose upper and lower limits, and (c) adjusting a subject's measured glucose level to an intracellular glucose level that correlates to an accepted normal lower intracellular glucose limit (LIGL) and the an normal upper intracellular glucose limit (UIGL).

First, using the accepted normal lower glucose limit (LGL) and the accepted normal glucose upper limit (AU), equations for a personalized lower glucose limit (GL) (Equations 12 and 13) and a personalized upper glucose limit (GU) (Equations 14 and 15) can be derived. Equations 13 and 15 are Equations 12 and 14 rewritten for when both a laboratory HbA1c and an aHbA1c are available.

$$GL = \frac{K_M * LGL}{\frac{k_{gly}^{sub}}{k_{gly}^{ref}} * K_M + LGL\left(\frac{k_{gly}^{sub}}{k_{gly}^{ref}} - 1\right)} \qquad \text{Equation 12}$$

where $$k_{gly}^{ref}$$

is the $k_{gly}$ for a normal person and $$k_{gly}^{sub}$$

is the subject's $k_{gly}$ $$GL = \frac{K_M * LGL * HbA1c(1 - aHbA1c)}{aHbA1c(1 - HbA1c) * K_M + LGL(aHbA1c - HbA1c)} \qquad \text{Equation 13}$$

$$GU = \frac{K_M * AU}{\frac{k_{gly}^{sub}}{k_{gly}^{ref}} * K_M + AU\left(\frac{k_{gly}^{sub}}{k_{gly}^{ref}} - 1\right)} \qquad \text{Equation 14}$$

$$GU = \frac{K_M * AU * HbA1c(1 - aHbA1c)}{aHbA1c(1 - HbA1c) * K_M + AU(aHbA1c - HbA1c)} \qquad \text{Equation 15}$$

Equations 12 and 14 are based on $k_{gly}$ because the higher and lower limits of a glucose range are based on an equivalent intracellular glucose level.

The currently accepted values for the foregoing are LGL=70 mg/dL, $$k_{gly}^{ref} = 6.2 * 10^{-6} \text{ dL} * \text{mg}^{-1} * \text{day}^{-1},$$

and AU=180 mg/dL.

Figure 6A:
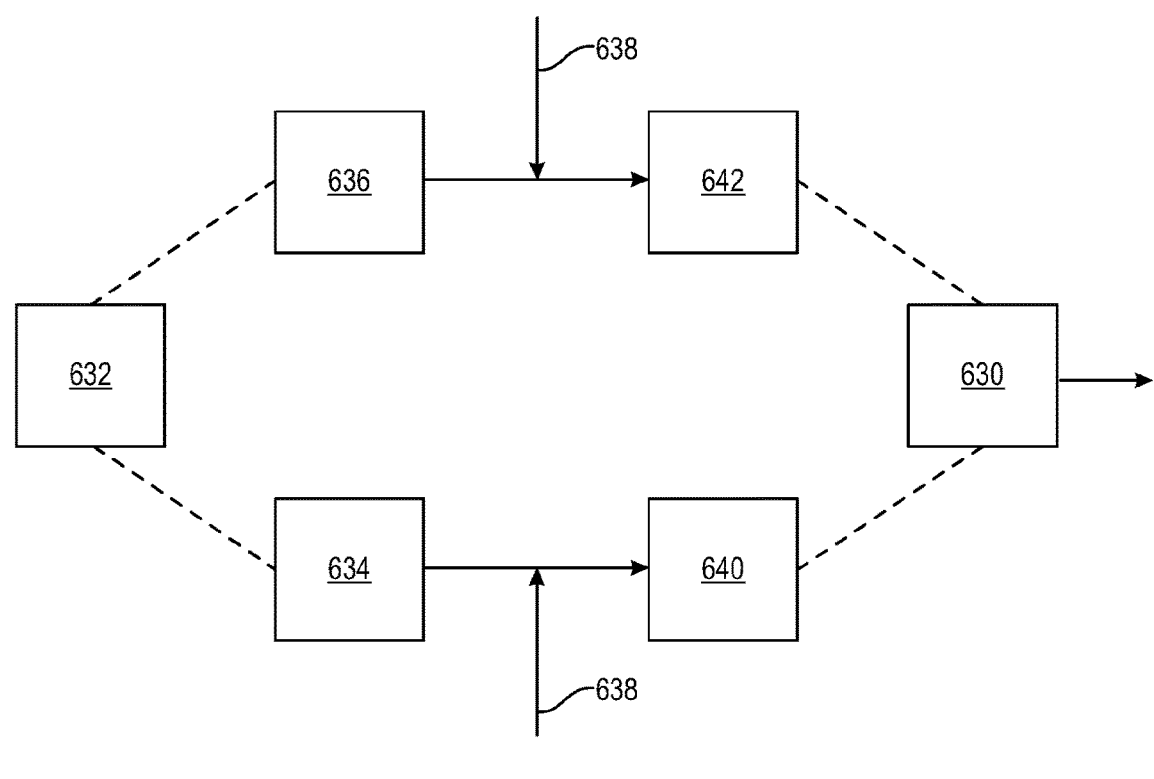
FIG. 6A illustrates an example of a method of determining a personalized-target glucose range in accordance with some of the embodiments of the present disclosure.

FIG. 6A illustrates an example of a method of determining a personalized-target glucose range 630. A desired glucose range 632 (e.g., the currently accepted glucose range) having a lower limit 634 and an upper limit 636 can be personalized using physiological parameter $k_{gly}$ 638 using Equation 12 and Equation 14, respectively. This results in a personalized lower glucose limit (GL) 640 (Equation 12±7%) and a personalized upper glucose limit (GU) 642 (Equation 14±7%) that define the personalized-target glucose range 630. Alternatively or in addition to the foregoing, a desired glucose range 632 (e.g., the currently accepted glucose range) having a lower limit 634 and an upper limit 636 can be personalized using a laboratory HbA1c and calculated aHbA1c 638 using Equation 13 and Equation 15, respectively. Therefore, methods may generally include, after (a) calculating $k_{gly}$ and/or (b) after measuring HbA1c and calculating aHbA1c, a personalized-target glucose range may be determined where the lower glucose limit may be altered according to Equation 12 (and/or Equation 13)±7% and/or the upper glucose limit may be altered according to Equation 14 (and/or Equation 15)±7%. For example, a subject with a $k_{gly}$ of 5.5*10⁻⁶ dL*mg⁻¹*day⁻¹ may have a personalized-target glucose range of about 81±7 mg/dL to about 219±27 mg/dL. Therefore, the subject may have a different range of acceptable glucose levels than the currently practiced glucose range.

Figure 6B:
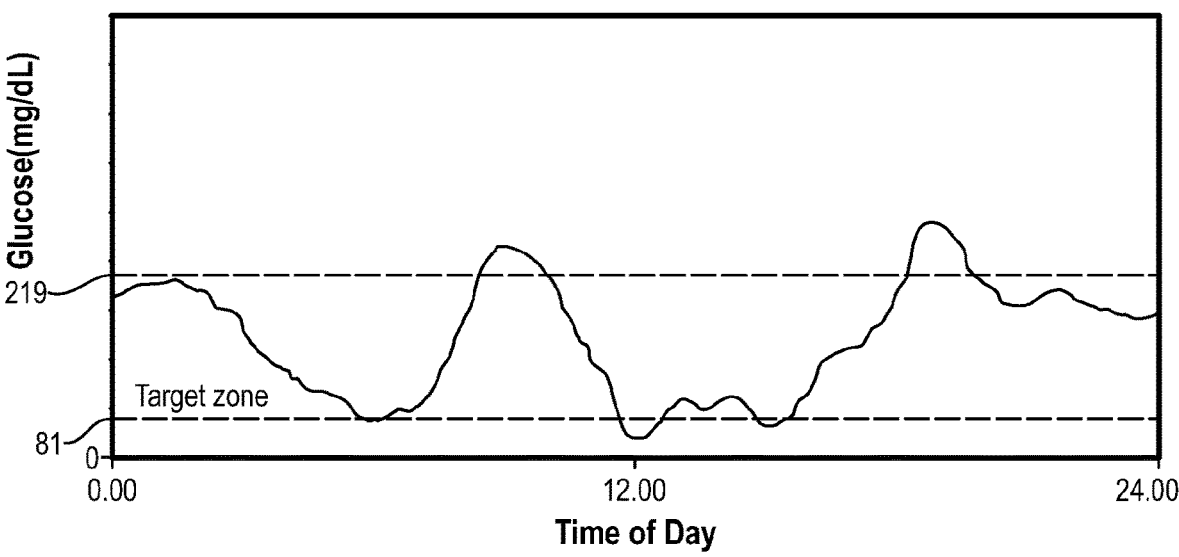
FIG. 6B illustrates an example of a personalized-target glucose range report that may be generated as an output by a physiological parameter analysis system in accordance with some of the embodiments of the present disclosure.

FIG. 6B, with reference to FIG. 3, illustrates an example of a personalized-target glucose range report that may be generated as an output 318 by a physiological parameter analysis system 310 of the present disclosure. The illustrated example report includes a plot of glucose level over a day relative to the foregoing personalized-target glucose range (shaded area). Alternatively, other reports may include, but are not limited to, an ambulatory glucose profile (AGP) plot, a numeric display of the personalized-target glucose range with the most recent glucose level measurement, and the like, and any combination thereof.

In another example, a subject with a $k_{gly}$ of $6.5*10^{-6}$ dL*mg$^{-1}$*day$^{-1}$ may have a personalized-target glucose range of about $66\pm5.5$ mg/dL to about $167\pm18$ mg/dL. With the much-reduced upper glucose level limit, the subject's personalized diabetes management may include more frequent glucose level measurements and/or medications to stay substantially within the personalized-target glucose range.

In yet another example, a subject with a $k_{gly}$ of $5.0*10^{-6}$ dL*mg$^{-1}$*day$^{-1}$ may have a personalized-target glucose range of about $92\pm8$ mg/dL to about $259\pm34$ mg/dL. This subject is more sensitive to lower glucose levels and may feel weak, hungry, dizzy, etc. more often if the currently practiced glucose range (70 mg/dL and 180 mg/dL) were used.

While the foregoing example all include a personalized glucose lower limit and a personalized glucose upper limit, personalized-target glucose range may alternatively include only the personalized glucose lower limit or the personalized glucose upper limit and use the currently practiced glucose lower or upper limit as the other value in the personalized-target glucose range.

In a second method for taking into account a subject's specific $k_{gly}$ with respect to a glucose reading and/or a corresponding personalized glucose range, a subject's plasma glucose level (e.g., as measured with an analyte sensor configured to measure a glucose level in a bodily fluid where said sensor may be a part of a larger system) is personalized to yield an effective plasma glucose (PG$_{eff}$) level using $k_{gly}$ per Equation 16.

$$PG_{eff} = \frac{r*PG*K_M}{K_m + (1-r)PG} \qquad \text{Equation 16}$$

$$\text{where } r = \frac{k_{gly}}{k_{gly}^{ref}}$$

The PG$_{eff}$ level may be used in combination with the accepted normal lower glucose limit and/or the accepted normal glucose upper limit for diagnosing, monitoring, and/or treating a subject. That is, the PG$_{eff}$ level is interpreted relative to the accepted glucose limits, which herein are considered between 70 mg/dL and 180 mg/dL but may change based on new clinical and/or scientific data and health officials' recommendations.

For example, a subject with a $k_{gly}$ of $6.5*10^{-6}$ dL*mg$^{-1}$*day$^{-1}$ may receive a measured glucose level of 170 mg/dL that, when Equation 16 is applied changes to 183 mg/dL, which is interpreted in context of the accepted glucose limits (70 mg/dL to 180 mg/dL). Therefore, currently, the subject would consider the measurement of 170 mg/dL to be within accepted limits. However, the effective plasma glucose is actually higher, which may impact the proper dose of insulin or other medication that should be delivered.

In a third method for taking into account a subject's specific $k_{gly}$ with respect to a glucose reading and/or a corresponding personalized glucose range, a subject's plasma glucose level (e.g., as measured with an analyte sensor configured to measure a glucose level in a bodily fluid where said sensor may be a part of a larger system) is personalized to an intracellular glucose (IG) level using $k_{gly}$ per Equation 17.

$$IG = \frac{k_{gly}*PG}{k_g\left(1 + \frac{PG}{K_M}\right)} \qquad \text{Equation 17}$$

The subject's IG level may then be compared to an accepted normal lower intracellular glucose limit (LIGL) and an accepted normal upper intracellular glucose limit (UIGL). The currently accepted values for LIGL and UIGL are 0.29 mg/dL and 0.59 mg/dL, respectively.

The personalized-target glucose range and/or personalized glucose level (e.g., an effective plasma glucose level or an intracellular glucose level) may be determined and/or implemented in a physiological parameter analysis system. For example, a set of instructions or program associated with a glucose monitor and/or health monitoring device that determines a therapy (e.g., an insulin dosage) may use a personalized-target glucose range and/or personalized glucose level in such analysis. In some instances, a display or subject interface with display may display the personalized-target glucose range and/or personalized glucose level.

The personalized-target glucose range and/or personalized glucose level may be updated over time as one or more physiological parameters are recalculated.

Personalized-Target Average Glucose

Equation 18 can be used to calculate a personalized-target average glucose level (GT) from a reference glucose target (RG). The reference target glucose can take any value that physician determines suitable, for example 120 mg/dL.

$$GT = \frac{K_M*RG}{\frac{k_{gly}^{sub}}{k_{gly}^{ref}}K_M + RG\left(\frac{k_{gly}^{sub}}{k_{gly}^{ref}} - 1\right)} \qquad \text{Equation 18}$$

Alternatively or in combination with Equation 18, Equation 19 can be used to calculate a GT based on a laboratory HbA1c and a calculated aHbA1c.

$$GT = \frac{K_M*RG*HbA1c(1 - aHbA1c)}{aHbA1c(1 - HbA1c)*K_M + RG(aHbA1c - HbA1c)} \qquad \text{Equation 19}$$

Alternatively or in combination with Equations 18 and/or 19, Equation 20 can be used to calculate a GT when the target HbA1c value (AT) is known.

$$GT = AT/(K(1 - AT)) \qquad \text{Equation 20}$$

In some embodiments, a physiological parameter analysis system may determine an average glucose level for the subject during time period 208 and, optionally, display the average glucose level and/or the target average glucose level. The subject may use the current average glucose level and the target average glucose level to self-monitor their progress over time period 208. In some instances, the current average glucose level may be transmitted (periodically or regularly) to a health care provider using a physiological parameter analysis system for monitoring and/or analysis.

Figure 7:
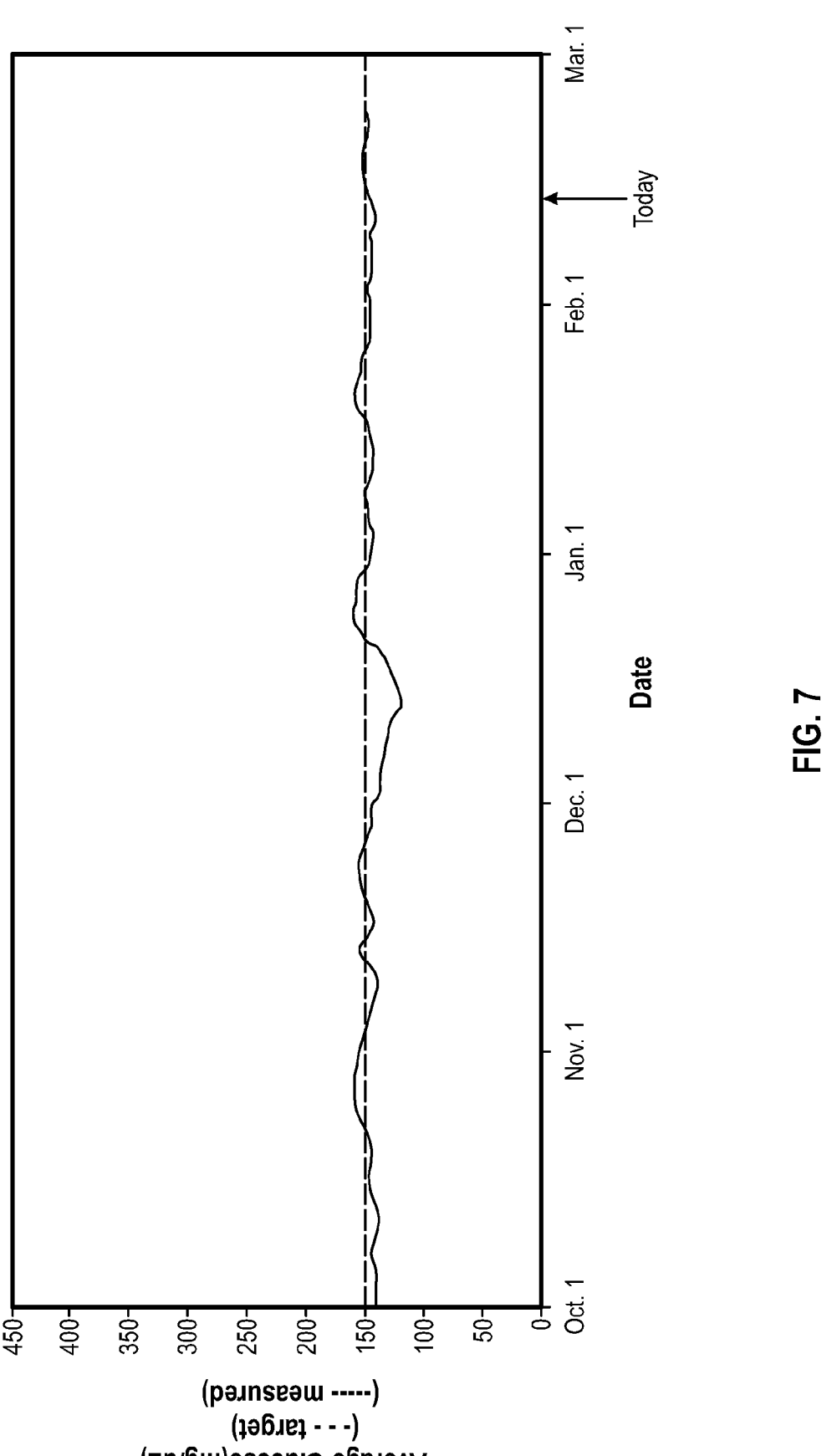
FIG. 7 illustrates an example of a personalized-target average glucose report that may be generated as an output by a physiological parameter analysis system in accordance with some of the embodiments of the present disclosure.

FIG. 7, with reference to FIG. 3, illustrates an example of a personalized-target average glucose report that may be generated as an output 318 by a physiological parameter analysis system 310 of the present disclosure. The illustrated example report includes a plot of a subject's average glucose (solid line) over time and the personalized-target average glucose (illustrated at 150 mg/dL, dashed line). Alternatively, other reports may include, but are not limited to, a numeric display of the personalized-target average glucose with the subject's average glucose level over a given time frame (e.g., the last 12 hours), and the like, and any combination thereof.

The personalized-target average glucose level may be updated over time as updated relevant physiological parameters, calculated values, and/or measured values for one or more of Equations 18-20 are obtained.

Personalized Treatment—Subject Triage

Insulin pumps along with continuous glucose monitoring may be used for subjects that need tight control of their glucose levels. As illustrated above, the target glucose range is individualized and based on $k_{gly}$. Therefore, in some instances, subjects with a narrower personalize-target glucose range may be stronger candidates for insulin pumps with continuous monitoring. Triage of subjects to be stronger candidates for insulin pumps along with continuous glucose monitoring may be based on a spread of the personalized-target glucose range, and $k_{gly}$.

The spread between currently practiced glucose lower or upper limit is about 110 mg/dL. However, as illustrated above, depending on $k_{gly}$ could narrow to about 60 mg/dL or less. Some embodiments may involve triaging a subject to an insulin pump with continuous glucose monitoring when the personalized-target glucose range span is below a threshold that is less than 110 mg/dL.

Some embodiments may involve triaging a subject to an insulin pump with continuous glucose monitoring when $k_{gly}$ exceed a threshold greater than $6.2 \times 10^{-6} \, dL \times mg^{-1} \times day^{-1}$.

Some embodiments may involve placing a subject to intense hypoglycemia prevention program when $k_{gly}$ is lower than a threshold, e.g. $6.2 \times 10^{-6} \, dL \times mg^{-1} \times day^{-1}$.

In some embodiments, triaging a subject to an insulin pump with continuous glucose monitoring may be a stepped triage where first a subject's glucose levels are monitored continuously for a reasonable time period (e.g., about 5 days, about 10 days, about 15 days, about 30 days, or more). This continuous monitoring time period can be used to assess if the subject is capable of managing glucose levels effectively or if an insulin pump is better, or required.

Whether the triaging is straight to an insulin pump with continuous glucose monitoring or a stepped triage with monitoring before treatment with the insulin pump may be determined by the level of the indicators (i.e., the personalized-target glucose range span, $k_{gly}$, or any combination thereof). For example, if $k_{gly}$ is about $6.4 \times 10^{-6} \, dL \times mg^{-1} \times day^{-1}$ and the personalized-target glucose range span is about 103 mg/dL, the subject may be more suited for a stepped triage as compared to another subject where the corresponding indicators suggest an insulin pump should be used.

In some embodiments, triage may be based on a lookup table (e.g., stored in a physiological parameter analysis system of the present disclosure). The lookup table may, for example, correlate multiple values to each other including, but not limited to, one or more physiological parameters ($k_{gly}$, $k_{age}$, and/or K), a personalized-target glucose range span, and/or other factors described herein like an existing medical condition, a family history of a medical condition, a current treatment, an age, a race, a gender, a geographic location, a diabetes type, a duration of diabetes diagnosis, and the like, and any combination thereof. Columns in the lookup table may, for example, define ranges or limits for the foregoing parameters, and the rows may indicate a suggested course of action, which may be an output 318 of a physiological parameter analysis system 310 of FIG. 3. For example, two columns may define an upper and lower bound of $k_{gly}$, where each row corresponds to a suggested course of action, such as "candidate for insulin pump," "candidate for closed-loop control system," "candidate for basal/bolus insulin therapy," "candidate for basal only insulin therapy," or any such treatment used to control diabetes or effect the subject's glycation. In some instances, more than one course of action may be indicated. Therefore, in this example, a subject triage report may simply display the suggested course(s) of action.

Alternatively, the subject triage report may, for example, show a map of zones corresponding to the course(s) of action on a plot defined by one or more of the parameters described above relative to the lookup table. Such zones may, in some instances, be defined by the lookup table, labeling each zone representing a recommendation and indicated the glycemic parameter point on the map to show the relevant zone for that subject.

While the two foregoing subject triage reports are examples based on lookup tables, alternatively, the two foregoing subject triage reports could be based on other correlations between (1) one or more physiological parameters ($k_{gly}$, $k_{age}$, and/or K), a personalized-target glucose range span, and/or other factors described herein and (2) a course(s) of action (e.g., a mathematical algorithm or matrix analysis).

As described, a subject's glycation parameters may help healthcare providers and payors to better determine what therapy tools are most appropriate for which subjects. For instance, closed-loop insulin pump systems are expensive to employ and maintain, but subjects who have a high glycation rate may have a very narrow personalized-target glucose range where the safest treatment is keeping their glucose levels within such ranges using a closed-loop insulin pump system.

In some embodiments, the insulin pumps along with continuous glucose monitoring may be closed-loop systems. In some embodiments, the insulin pumps along with continuous glucose monitoring may be hybrid-loop systems. For example, referring back to FIG. 4, a physiological parameter analysis system may further include one of the foregoing insulin pumps communicable with one or more of the components in the physiological parameter analysis system 410, for example, the glucose monitor 424 (e.g., a continuous glucose monitoring system) and health monitoring device 420.

Personalize Treatment—Titration of Diabetes Medication

In some embodiments, one or more physiological parameters ($k_{gly}$, $k_{age}$, and K) may be used in titrating dosages of diabetes medication (e.g., insulin) to a subject. For example, referring to FIG. 3, a physiological parameter analysis system 310 of the present disclosure may determine or have input (1) one or more physiological parameters, (2) a personalized-target glucose range, (3) a personalized glucose level (e.g., an effective plasma glucose level or an intracellular glucose level), and/or (4) a personalized-target average glucose. Then, when a subsequent glucose level is measured the physiological parameter analysis system 310 may output a recommended diabetes medication dosage. An alternative or complimentary output 318 may be a glucose pattern insight report.

Examples of glucose pattern insight reports can be found in US Patent Application Publication Nos. 2014/0188400 and 2014/0350369, each incorporated herein by reference. The disclosed analyses and reports in the forgoing applications may be modified based on the one or more physiological parameters ($k_{gly}$, $k_{age}$, and K) of the present disclosure.

Figure 8:
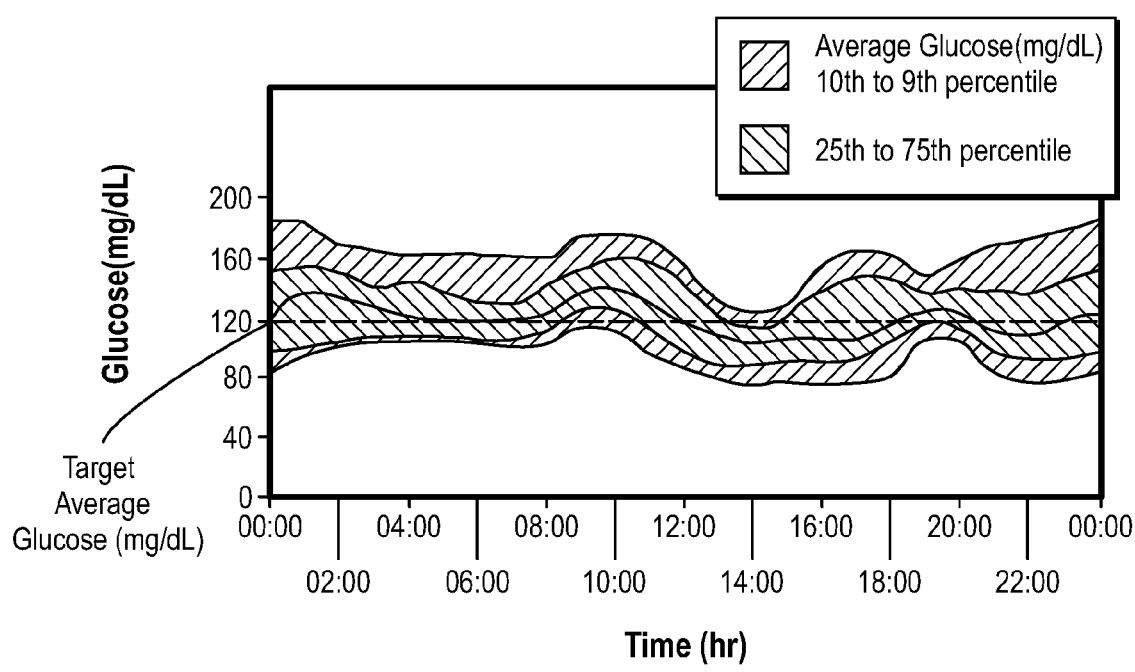
FIG. 8 illustrates an example of a glucose pattern insight report that may be generated as an output by a physiological parameter analysis system in accordance with some of the embodiments of the present disclosure.

For example, FIG. 8, with reference to FIG. 3, illustrates an example of a glucose pattern insight report that may be an output 318 of a physiological parameter analysis system 310 (e.g., an insulin titration system). The illustrated glucose pattern insights report incorporates an AGP along with a table of glycemic control measures (or "traffic lights"). As illustrated, the report includes an AGP plot over an analysis time period (e.g., about one to about four months) that illustrates the personalized-target average glucose at 120 mg/dL, the average glucose levels for the subject over the analysis time period, the $25^{th}$ to $75^{th}$ percentile of glucose levels for the subject over the analysis time period, and the $10^{th}$ to $90^{th}$ percentile of glucose levels for the subject over the analysis time period. Optionally, the glucose pattern insight report may further or alternatively display the personalized-target glucose range and/or personalized glucose level (e.g., an effective plasma glucose level or an intracellular glucose level) relative to the currently accepted glucose range. Additionally, the glucose pattern insight report may optionally further include one or more of: a laboratory HbA1c level, a cHbA1c level, an adjusted HbA1c level based on either laboratory HbA1c or glucose data, the date range over which the average glucose and related percentiles were determine, and the like.

Below the AGP plot on the glucose pattern insight report is the table that correlates one or more (illustrated as three) glycemic control measures to a subject's average glucose levels for a given shortened time period of the day over the analysis time period. The correlation displays, in this example, as traffic lights (e.g., green (good), yellow (moderate), or high (red)) that correspond to the risk of a condition based on the glycemic control measures. Examples of glycemic control measures include, but are not limited to, likelihood of low glucose, likelihood of high glucose, the proximity of the average glucose to the personalized-target average glucose, the adherence of the glucose levels to the personalized-target glucose range and/or the personalized glucose level relative to the currently accepted glucose range, the degree of variability of the average glucose below (or above) to the personalized-target average glucose, the degree of variability of the glucose levels outside (below and/or above) the personalized-target glucose range and/or the personalized glucose level relative to the currently accepted glucose range, and the like.

In some embodiments, the glucose pattern insights report may be used as part of a diabetes medication titration system, where the traffic lights (or values associated therewith) can drive logic to provide treatment modifications such as changing basal dosages of the diabetes medication or bolus amounts of the diabetes medication associated with meals. For example, when used in conjunction with an automatic or semi-automatic system for titration, the logic driving these traffics lights may provide recommendations to subjects on dosage adjustments.

The glucose pattern insights report and related analyses that incorporate the use of the kinetic model described herein may provide better treatment to subjects with diabetes. For this example, as described above, a subject with a $k_{gly}$ of $5.1*10^{-6}$ dL*mg$^{-1}$*day$^{-1}$ may have a personalized-target glucose range of about 90±8 mg/dL to about 250±32 mg/dL. This subject is more sensitive to lower glucose levels and may feel weak, hungry, dizzy, etc. more often if the currently practiced glucose range (70 mg/dL and 180 mg/dL) were used. The analytical logic used for the glucose pattern insights report described herein that uses one or more physiological parameters ($k_{gly}$, $k_{age}$, and K) may include settings that define the risk of hypoglycemia as traffic lights for "likelihood of low glucose." For example, if the likelihood of low glucose indicates low risk (e.g., a green traffic light), then it is considered safe to increase insulin. If the likelihood of low glucose indicates moderate risk (e.g., yellow traffic light), then it is considered that the current risk is acceptable but no further increase of insulin should be made. Finally, if the likelihood of low glucose indicates high risk, then it is recommended that insulin should be reduced to get the glucose back to tolerable levels. For a subject with high risk of hypoglycemia because of an increase lower glucose level threshold, the amount of risk associated with moderate and high risk (e.g., how far below the lower glucose level threshold) may be less than a subject with a normal lower glucose level threshold.

While the foregoing example discusses a glucose pattern insights report as the output 318, other outputs using the same logic and analyses may be used in other embodiments. For example, the output 318 may be values of dosage recommendations.

The one or more physiological parameters ($k_{gly}$, $k_{age}$, and K) and related analyses (e.g., personalized-target glucose range, personalized glucose level, personalized-target average glucose, cHbA1c, aHbA1c, and the like) may be updated periodically (e.g., about every 3 months to annually). The frequency of updates may depend on, among other things, the subject's glucose level and diabetes history (e.g., how well the subject stays within the prescribed thresholds), other medical conditions, and the like.

An insulin titration system may optionally also utilize error associated with the one or more physiological parameters ($k_{gly}$, $k_{age}$, and K). Error values can be determine using standard statistically techniques by those skilled in the art and may be used as another set of parameters for configuring the titration system. For example, the titration system may use the reduced amount of risk for hypoglycemia (i.e., a smaller tolerance to be below the lower glucose level threshold for indicating moderate and high risk) may be implemented when the lower glucose level of the personalized-target glucose range of about 75 mg/dL with an error of about 7% or less.

The dosage of diabetes mediation (e.g., via titration) may be updated over time as one or more physiological parameters are recalculated.

Closed-Loop and Hybrid Closed-Loop Control Systems

Closed-loop systems and hybrid closed-loop systems that recommend or administer insulin dosages to a subject have been developed for insulin delivery based on near real-time glucose readings. These systems are often based on models describing the subject's physiology, glucose sensor dynamics, and glucose sensor error characteristics. In some embodiments, the one or more physiological parameters ($k_{gly}$, $k_{age}$, and K) and related analyses (e.g., personalized-target glucose range, personalized glucose level, personalized-target average glucose, cHbA1c, aHbA1c, and the like) may be incorporated into the closed-loop system, similarly to what was described above for insulin titration, in order to better meet the needs of the subject.

Closed-loop systems often are configured to "drive" the subject's glucose levels inside a target range and/or toward a single glucose target, which may be the personalized-target glucose range, the personalized glucose level relative to the accepted target glucose range, and/or the personalized-target average glucose described herein. For example, for a subject with high $k_{gly}$ and an increased lower glucose limit for their personalized-target glucose range, the controller may drive their glucose levels in a way to stay above the lower glucose limit based on $k_{gly}$, which avoids lower glucose levels that adversely affect them more than subjects with a normal glucose range. Similarly, subjects with reduced upper glucose limits for their personalized-target glucose range may have the controller of a closed-loop insulin delivery system and hybrid closed-loop insulin delivery system drive glucose to stay below the personalized-upper glucose limit to mitigate hyperglycemic effects.

The metrics by which a closed-loop insulin delivery system and hybrid closed-loop insulin delivery system determine a dosage of insulin may be updated over time as one or more physiological parameters are recalculated. For example, the personalized-target glucose range, personalized glucose level, and/or personalized-target average glucose may be updated when one or more physiological parameters are recalculated.

Personalized Treatment—Glycation Medication

Diabetes is a disease caused by a subject's pancreas being unable to produce sufficient (or any) insulin. However, in some instances, a subject's glycation process may be the source of the body not properly controlling intracellular glucose. Such subjects may be more responsive to treatments that use glycation medications (e.g., azathioprine, meloxicam, nimesulide, piroxicam, mefenamic acid, oxaprozin, D-penicillamine, penicillin G, trimethylphloroglucinol, ranitidine, phloroglucinol dihydrate, epinephrine bitartrate, pyridoxine HCl, toiramate, escitalopram, hydroquinone, tretinoin, colchicine, rutin, and the like) rather than traditional diabetes treatments. The kinetic model of the present disclosure derives $k_{gly}$ and/or K (which is based in part on $k_{gly}$). Therefore, one or both of these physiological parameters may be used in identifying, treating, and/or monitoring a subject with a glycation disorder.

Some embodiments may involve monitoring $k_{gly}$ and/or K for a subject on glycation medication and, optionally, changing a glycation medication dosage based on changes to $k_{gly}$ and/or K. For example, referring to FIG. 2, some embodiments may involve determining $k_{gly1}$ and/or $K_1$ at a time $t_1$ and a corresponding $k_{gly2}$ and/or $K_2$ at time $t_2$ (as described above) and treating a subject with glycation medication over time period 208. Then, based on a comparison of $k_{gly1}$ and/or $K_1$ to the corresponding $k_{gly2}$ and/or $K_2$, a dosage and/or type of glycation medication may be altered for a subsequent time period. Then, in some instances, a corresponding $k_{gly3}$ and/or $K_3$ may be determined at the end of the subsequent time period for comparison to one or more of the previously determined physiological parameters. The time between $t_1$ and $t_2$ and between $t_2$ and $t_3$ should be at least the expected time for the glycation medication to make a measurable change in the parameter being monitored, which may depend on the medication and the dosage.

In some embodiments, an output 318 of the physiological parameter analysis system 310 of FIG. 3 may be a glycation medication report that includes glycation medication and/or dosage recommendations based on $k_{gly}$ and/or K calculated by the physiological parameter analysis system 310. This output 318 may be displayed for a subject, healthcare provider, and/or the like to review and adjust the glycation medication and/or dosage.

Alternatively, the dosage recommendations provide a subject and/or automated medication delivery system with the next dosage to be administered. Here, the system guides titration of the medication, where the subject may start with the lowest dosage or a recommended initial dosage. The initial dosage may be defined by the current condition of the subject, the subject's $k_{gly1}$ and/or $K_1$, and other factors described herein. After an appropriate amount of time has passed for the effects of the current medication dosage to be adequately determined, $k_{gly2}$ and/or $K_2$ can be determined based on a new laboratory HbA1c level and the glucose levels measured during the medication dosage. $k_{gly2}$ and/or $K_2$ may then be compared to (1) $k_{gly1}$ and/or $K_1$ and/or (2) a target $k_{gly}$ and/or a target K to determine if the dosage needs to be changed. For example, for a high glycator subject taking a medication is intended to lower glycation rate, if $k_{gly2}$ is still higher than desired, then the dosage recommendation may be increased according to (1) standard titration protocols and/or (2) a system that accounts for how past dosage changes affect the subject (known as control theory). In another example, if the subject's $k_{gly2}$ is low, then the dosage may be decreased. Medications could also be similarly titrated to affect K or other parameters. In addition, a similar process could be used to recommend non-medication treatments such as blood transfusion or harvesting by guiding the appropriate amount of blood to be affected.

Using $k_{gly}$ and/or K to monitor glycation medication efficacy and titration is valuable to healthcare providers for treating subjects with abnormal glycation physiology.

The metrics by which a dosage of glycation medication is determined may be updated over time as one or more physiological parameters are recalculated.

Identifying Abnormal or Diseased Physiological Condition

The kinetic modeling, in certain embodiments, provides physiological parameters (e.g., $k_{gly}$, $k_{age}$ (or $k_{gen}$), and/or K) for different time periods, where the same parameter is compared between the different time periods to indicate abnormal or disease state of the subject. Variation in the $k_{gly}$, $k_{age}$, and/or K in subjects may provide an indication of abnormal or disease condition of the subject. That is, while $k_{gly}$, $k_{age}$, and/or K varies between subjects, a variation in $k_{gly}$, $k_{age}$, and/or K for a single individual are small and slow. Thus, a comparison of $k_{gly}$, $k_{age}$, and/or K at two or more different time periods provides physiological condition information of the subject. For example, when a clinically significant change to $k_{gly}$, $k_{age}$, and/or K is observed over time an abnormal or diseased physiological condition may, and likely, exists.

For example, when $k_{gly}$ significantly varies over time such that the variation is clinically significant, such clinically significant variation can indicate that the glucose transporter level or cell membrane has changed. Such biological changes may indicate a potential metabolic change in the subject's body resulting from the subject's physiology under-going a disease state.

When $k_{age}$ and/or $k_{gen}$ varies significantly over time such that the variation is clinically significant, such clinically significant variation can indicate changes to the subject's immune system because the immune system is designed to recognize cells that need to be removed.

A clinically significant variation in $k_{age}$ and/or $k_{gen}$ may also or alternatively be associated with the oxygen sensing mechanism in the body. An increasing $k_{age}$ and/or $k_{gen}$ over time may indicate that the subject's body needs the red blood cells to carry more oxygen or the oxygen sensing mechanism is not functioning correctly, either reason indicating a physiological state change such as for example, blood loss or a disease condition.

In yet another example (in combination or alternative of the foregoing examples), clinically significant variation in $k_{age}$ and/or $k_{gen}$ may be associated with bone marrow changes. For example, if the bone marrow suddenly produces a lot more oxygen carrying red blood cells, the subject's body will respond by killing off or eliminating more red blood cells. That is, a clinically significant increase in $k_{age}$ and/or $k_{gen}$ may be associated with bone marrow abnormality.

In another example, a hormone disorder can cause a clinically significant variation in $k_{age}$, $k_{gen}$, and K. Hormones can affect heart rate, contraction strength, blood volume, blood pressure, and red blood cell production. Stress hormones such as catecholamines and cortisol stimulate the release of reticulocytes from the bone marrow and possibly also enhance erythropoiesis. Therefore, large fluctuation on hormone level can change $k_{age}$ and/or $k_{gen}$, and consequently K.

In yet another example, deviations from normal of the $k_{gly}$, $k_{age}$, and/or K may be an indicator of diabetes or pre-diabetes. Using $k_{gly}$, $k_{age}$, and/or K to measure diabetes or pre-diabetes may be more effective than standard fasting glucose tests and laboratory HbA1c. For instance, a subject with a laboratory HbA1c value in the normal range and normal fasting glucose may have low $k_{gly}$ associated with high glucose values at times in the day other than fasting. Therefore, the subject may be a candidate for earlier diabetes intervention that otherwise may have gone unnoticed based on standard diabetes diagnoses methods.

In another example, for a subject with a newly high laboratory HbA1c, the standard diabetes treatments may be employed to lower their HbA1c. However, determining that $k_{gly}$ is abnormal may be an indication that the problem with their glycation physiology rather than their pancreas, suggesting other more targeted forms of treatment.

Embodiments of the present disclosure include displaying the determined $k_{gly}$, $k_{age}$, and/or K, the changes in $k_{gly}$, $k_{age}$, and/or K over time, and/or possible abnormal or diseased physiological conditions.

In the manner described herein, in accordance with the embodiments of the present disclosure, the physiological parameter analysis provides an indication of a subject's abnormal or disease condition, as well as an analysis and/or monitoring tool for one or more parameters or characteristics for a subject's personalized diabetes management.

Identifying Supplements and/or Medicines

Several supplements and medications interact with the kinetics of red blood cell glycation, elimination, and generation within the body. For example, supplements and medicines used by athletes to dope include, but are not limited to, human growth hormones, supplements and medicines that increase metabolic levels, and the like. Human growth hormones can increase red blood cell count and, consequently, increase $k_{age}$. In another example, supplements and medicines that increase metabolic levels (e.g., exercise mimetics like AMPK agonists) can affect $k_{gly}$. Therefore, some embodiments may use one or more physiological parameters ($k_{gly}$, $k_{age}$, and/or K) as an indicator of doping.

In a first example, having one or more physiological parameters ($k_{gly}$, $k_{age}$, and/or K) outside normal ranges may be used, in some instances, as an indicator of doping.

In another example, once the one or more physiological parameters ($k_{gly}$, $k_{age}$, and/or K) are determined, continuous monitoring over a 10-day or longer period could identify sudden changes in the physiological parameters that could indicated doping. This could be used alone or in combination with the foregoing example of the one or more physiological parameters being outside normal ranges.

Physiological Age

The physiological parameters $k_{age}$ and, consequently, K change due to aging. Therefore, $k_{age}$ and/or K (provided a stable or known change in $k_{gly}$) may be used as biological markers to calculate a standardized metabolic age. Generally, over time, $k_{age}$ decreases and K increases. Using a correlation between $k_{age}$ and/or K and age in healthy subjects, a new subject's metabolic age may be calculated. This metabolic age may then be used as an indicator of the new subject's risk for age-related degenerative conditions like heart disease, Alzheimer's, or osteoperosis. The risk for age-related degenerative conditions may be used in conjunction with family history of age-related degenerative conditions for proactive screening and/or preventive treatment. For example, a 54-year old subject with a metabolic age of 65 with a family history of cardiovascular disease developing later in life may be tested more often for signs and/or progression of cardiovascular disease than a 54-year old subject with a metabolic age of 50 and a similar family history.

Analyte Monitors and Monitoring Systems

Generally, embodiments of the present disclosure are used with or as systems, devices, and methods for measuring glucose and, optionally, at least one other analyte in a bodily fluid. The embodiments described herein can be used to monitor and/or process information regarding glucose and, optionally, at least one other analyte. Other analytes that may be monitored include, but are not limited to, glucose derivatives, HbA1c, reticulocyte count, RBC GLUT1 level, acetyl choline, amylase, bilirubin, cholesterol, chorionic gonadotropin, creatine kinase (e.g., CK-MB), creatine, creatinine, DNA, fructosamine, glutamine, growth hormones, hormones, ketones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In embodiments that monitor glucose and one or more than one analytes, each of the analytes may be monitored at the same or different times.

The analyte monitors and/or analyte monitoring systems (referred to herein collectively as analyte monitoring systems) used with or as systems, devices, and methods for measuring glucose and, optionally, one or more analytes in a bodily fluid may be in vivo analyte monitoring systems or in vitro analyte monitoring systems. In some instances, systems, devices, and methods of the present disclosure may use both in vivo analyte monitoring systems and in vitro analyte monitoring systems.

In vivo analyte monitoring systems include analyte monitoring systems where at least a portion of an analyte sensor is, or can be, positioned in the body of a subject to obtain information about at least one analyte of the body. In vivo analyte monitoring systems can operate without the need for a factory calibration. Examples of in vivo analyte monitoring systems include, but are not limited to, continuous analyte monitoring systems and flash analyte monitoring systems.

Continuous analyte monitoring systems (e.g., continuous glucose monitoring systems), for example, are in vivo systems that can transmit data from a sensor control device to a reader device repeatedly or continuously without prompting (e.g., automatically according to a schedule).

Flash analyte monitoring systems (or flash glucose monitoring systems or simply flash systems), for example, are in vivo systems that can transfer data from a sensor control device in response to a scan or request for data by a reader device, such as with a near field communication (NFC) or radio frequency identification (RFID) protocol.

In vivo analyte monitoring systems can include a sensor that, while positioned in vivo, makes contact with the bodily fluid of the subject and senses one or more analyte levels contained therein. The sensor can be part of a sensor control device that resides on the body of the subject and contains the electronics and power supply that enable and control the analyte sensing. The sensor control device, and variations thereof, can also be referred to as a "sensor control unit," an "on-body electronics" device or unit, an "on-body" device or unit, or a "sensor data communication" device or unit, to name a few. As used herein, these terms are not limited to devices with analyte sensors, and encompass devices that have sensors of other types, whether biometric or non-biometric. The term "on body" refers to any device that resides directly on the body or in close proximity to the body, such as a wearable device (e.g., glasses, watch, wristband or bracelet, neckband or necklace, etc.).

In vivo analyte monitoring systems can also include one or more reader devices that receive sensed analyte data from the sensor control device. These reader devices can process and/or display the sensed analyte data, in any number of forms, to the subject. These devices, and variations thereof, can be referred to as "handheld reader devices," "reader devices" (or simply, "readers"), "handheld electronics" (or handhelds), "portable data processing" devices or units, "data receivers," "receiver" devices or units (or simply receivers), "relay" devices or units, or "remote" devices or units, to name a few. Other devices such as personal computers have also been utilized with or incorporated into in vivo and in vitro monitoring systems.

For example, referring to FIG. 4, a sensor or portion thereof of an in vivo analyte monitoring system may be the glucose monitor 424, and the reader device may be the health monitoring device 420. In alternative embodiments, the in vivo analyte monitoring system may be, in whole, the glucose monitor 424 that transmits data to a health monitoring device 420, data network 422, data processing terminal/PC 426, and/or server/cloud 428.

For in vivo analyte monitoring systems, the determination of one or more physiological parameters (e.g., $k_{gly}$, $k_{age}$ (or $k_{gen}$), and/or K) and/or other analyses described herein may be performed within the in vivo analyte monitoring system, in some instances. Only the physiological parameters may, for example, be determined within the in vivo analyte monitoring system and transmitted to a suitable other component of a physiological parameter analysis system, which may perform other analyses described herein. In some embodiments, the in vivo analyte monitoring system may only produce output signals that correspond to glucose levels that are received by another component of a physiological parameter analysis system. In such cases, one or more of the other component(s) of the physiological parameter analysis system may determine one or more physiological parameters (e.g., $k_{gly}$, $k_{age}$ (or $k_{gen}$), and/or K) and, optionally, perform one or more of the other analyses described herein.

Figure 9:
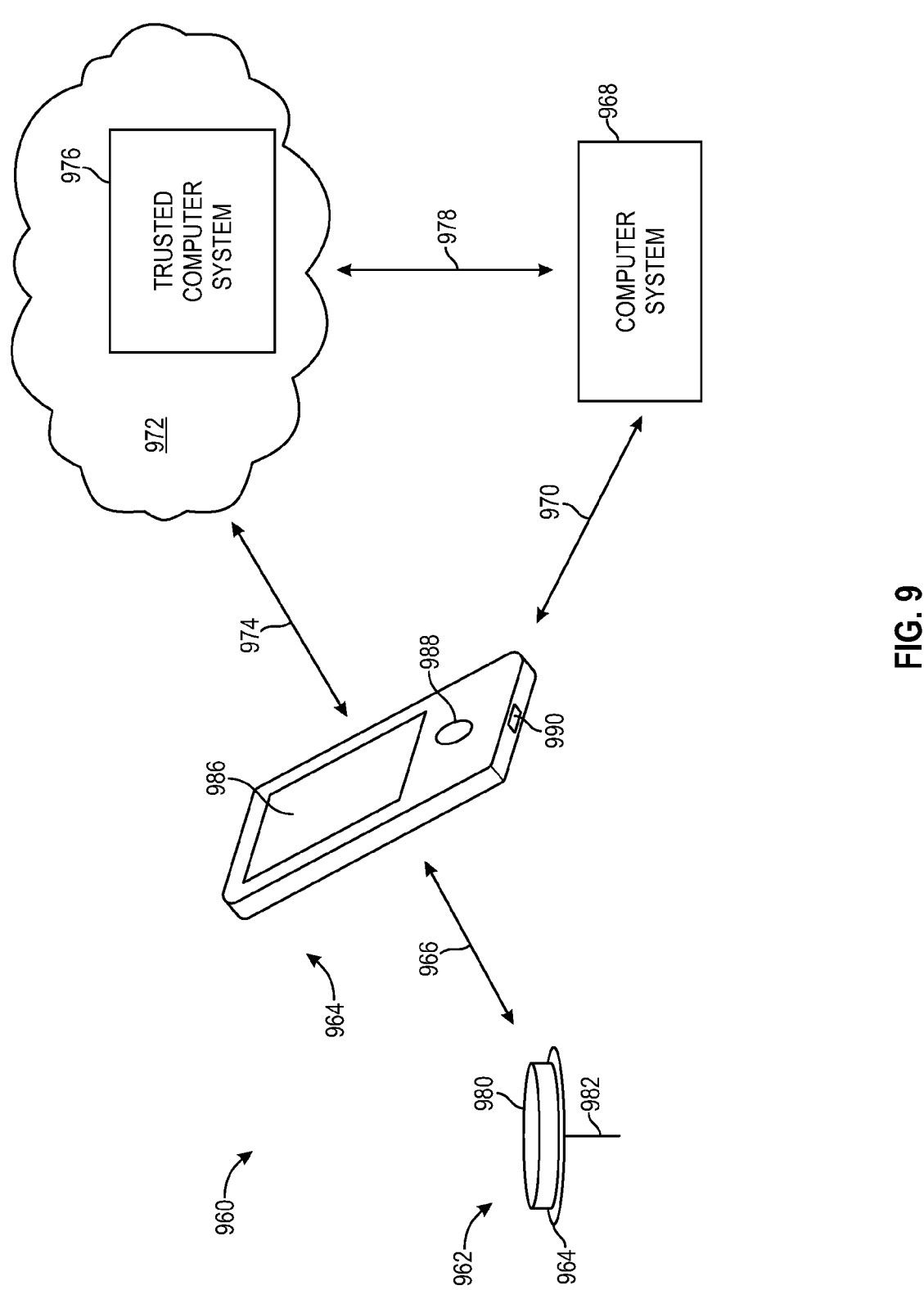
FIG. 9 illustrates an example of an in vivo analyte monitoring system in accordance with some of the embodiments of the present disclosure.

FIG. 9 illustrates an example of an in vivo analyte monitoring system 960. For embodiments of the present disclosure this example in vivo analyte monitoring system 960 monitors glucose and, optionally, one or more other analytes.

The in vivo analyte monitoring system 960 comprises a sensor control device 962 (which may be at least a portion of the glucose monitor 424 of FIG. 4) and a reader device 964 (which may be at least a portion of the health monitoring device 420 of FIG. 4) that communicate with each other over a local communication path (or link) 966, which can be wired or wireless, and uni-directional or bi-directional. In embodiments where path 966 is wireless, a near field communication (NFC) protocol, RFID protocol, BLUETOOTH® or BLUETOOTH® Low Energy protocol, WiFi protocol, proprietary protocol, or the like can be used, including those communication protocols in existence as of the date of this filing or their later developed variants.

Reader device 964 (e.g., a dedicated reader, a cellular phone or PDA running an app, or the like) is also capable of wired, wireless, or combined communication with a computer system 968 (which may be at least a portion of the data processing terminal/PC 426 of FIG. 4) over communication path (or link) 970 and with a network 972 (which may be at least a portion of the data network 422 and/or the server/cloud 428 of FIG. 4), such as the internet or the cloud, over communication path (or link) 974. Communication with network 972 can involve communication with trusted computer system 976 within network 972, or though network 972 to computer system 968 via communication link (or path) 978. Communication paths 970, 974, and 978 can be wireless, wired, or both, can be uni-directional or bi-directional, and can be part of a telecommunications network, such as a Wi-Fi network, a local area network (LAN), a wide area network (WAN), the internet, or other data network. In some cases, communication paths 970 and 974 can be the same path. All communications over paths 966, 970, and 974 can be encrypted and sensor control device 962, reader device 964, computer system 968, and trusted computer system 976 can each be configured to encrypt and decrypt those communications sent and received.

Variants of devices 962 and 964, as well as other components of an in vivo-based analyte monitoring system that are suitable for use with the system, device, and method embodiments set forth herein, are described in US Patent Application Publication No. 2011/0213225 (the '225 Publication), which is incorporated by reference herein in its entirety for all purposes.

Sensor control device 962 can include a housing 980 containing in vivo analyte monitoring circuitry and a power source. In this embodiment, the in vivo analyte monitoring circuitry is electrically coupled with an analyte sensor 982 that extends through an adhesive patch 984 and projects away from housing 980. Adhesive patch 984 contains an adhesive layer (not shown) for attachment to a skin surface of the body of the subject. Other forms of body attachment to the body may be used, in addition to or instead of adhesive.

Sensor 982 is adapted to be at least partially inserted into the body of the subject, where it can make fluid contact with that subject's bodily fluid (e.g., subcutaneous (subdermal) fluid, dermal fluid, or blood) and be used, along with the in vivo analyte monitoring circuitry, to measure analyte-related data of the subject. Sensor 982 and any accompanying sensor control electronics can be applied to the body in any desired manner. For example, an insertion device (not shown) can be used to position all or a portion of analyte sensor 982 through an external surface of the subject's skin and into contact with the subject's bodily fluid. In doing so, the insertion device can also position sensor control device 962 with adhesive patch 984 onto the skin. In other embodiments, insertion device can position sensor 982 first, and then accompanying sensor control electronics can be coupled with sensor 982 afterwards, either manually or with the aid of a mechanical device. Examples of insertion devices are described in US Patent Application Publication Nos. 2008/0009692, 2011/0319729, 2015/0018639, 2015/0025345, and 2015/0173661, all which are incorporated by reference herein in their entireties and for all purposes.

After collecting raw data from the subject's body, sensor control device 962 can apply analog signal conditioning to the data and convert the data into a digital form of the conditioned raw data. In some embodiments, this conditioned raw digital data can be encoded for transmission to another device (e.g., reader device 964), which then algorithmically processes that digital raw data into a final form representative of the subject's measured biometric (e.g., a form readily made suitable for display to the subject or readily used in the analysis module 420B of FIG. 4). This algorithmically processed data can then be formatted or graphically processed for digital display to the subject. In other embodiments, sensor control device 962 can algorithmically process the digital raw data into the final form that is representative of the subject's measured biometric (e.g., analyte level) and then encode and wirelessly communicate that data to reader device 964, which in turn can format or graphically process the received data for digital display to the subject. In other embodiments, sensor control device 962 can graphically process the final form of the data such that it is ready for display, and display that data on a display of sensor control device 962 or transmit the data to reader device 964. In some embodiments, the final form of the biometric data (prior to graphic processing) is used by the system (e.g., incorporated into a diabetes monitoring regime) without processing for display to the subject. In some embodiments, sensor control device 962 and reader device 864 transmit the digital raw data to another computer system for algorithmic processing and display.

Reader device 964 can include a display 986 to output information to the subject (e.g., one or more physiological parameter or an output derived therefrom like cHbA1c) and/or to accept an input from the subject, and an optional input component 988 (or more), such as a button, actuator, touch sensitive switch, capacitive switch, pressure sensitive switch, jog wheel or the like, to input data, commands, or otherwise control the operation of reader device 964. In certain embodiments, display 986 and input component 988 may be integrated into a single component, for example, where the display can measure the presence and location of a physical contact touch upon the display, such as a touch screen subject interface (which may be at least a portion of the subject interface 420A of FIG. 4). In certain embodiments, input component 988 of reader device 964 may include a microphone and reader device 964 may include software configured to analyze audio input received from the microphone, such that functions and operation of the reader device 964 may be controlled by voice commands. In certain embodiments, an output component of reader device 964 includes a speaker (not shown) for outputting information as audible signals. Similar voice responsive components such as a speaker, microphone and software routines to generate, process, and store voice driven signals may be included in sensor control device 962.

Reader device 964 can also include one or more data communication ports 990 for wired data communication with external devices such as computer system 968.

Example data communication ports 990 include, but are not limited to, USB ports, mini USB ports, USB Type-C ports, USB micro-A and/or micro-B ports, RS-232 ports, Ethernet ports, Firewire ports, or other similar data communication ports configured to connect to the compatible data cables. Reader device 964 may also include an integrated or attachable in vitro glucose meter, including an in vitro test strip port (not shown) to receive an in vitro glucose test strip for performing in vitro blood glucose measurements.

Reader device 964 can display the measured biometric data wirelessly received from sensor control device 962 and can also be configured to output alarms (e.g., a visual alarm on a display, an auditory alarm, or a combination thereof), alert notifications, glucose levels, etc., which may be visual, audible, tactile, or any combination thereof. Further details and other display embodiments can be found in US Patent Application Publication No. 2011/0193704, for example, which is incorporated herein by reference in its entirety for all purposes.

Reader device 964 can function as a data conduit to transfer the measured data from sensor control device 962 to computer system 968 or trusted computer system 976. In certain embodiments, the data received from sensor control device 962 may be stored (permanently or temporarily) in one or more memories of reader device 964 prior to uploading to computer system 968, trusted computer system 976, or network 972.

Computer system 968 may be a personal computer, a server terminal, a laptop computer, a tablet, or other suitable data processing device. Computer system 968 can be (or include) software for data management and analysis and communication with the components in analyte monitoring system 960. Computer system 968 can be used by the subject, a medical professional, or other user to display and/or analyze the biometric data measured by sensor control device 962. In some embodiments, sensor control device 962 can communicate the biometric data directly to computer system 968 without an intermediary such as reader device 964, or indirectly using an internet connection (also optionally without first sending to reader device 964). Operation and use of computer system 976 is further described in the '225 Publication incorporated herein. Analyte monitoring system 960 can also be configured to operate with a data processing module (not shown), also as described in the incorporated '225 Publication.

Trusted computer system 976 can be within the possession of the manufacturer or distributor of sensor control device 962, either physically or virtually through a secured connection, and can be used to perform authentication of sensor control device 962, for secure storage of the subject's biometric data, and/or as a server that serves a data analytics program (e.g., accessible via a web browser) for performing analysis on the subject's measured data.

In vivo analyte monitoring systems can be used in conjunction with or as a portion of an integrated diabetes management system. For example, an integrated diabetes management system may include an in vivo analyte monitoring system and a supplement/medication delivery system, and more specifically, an in vivo glucose monitoring system and an insulin delivery system (e.g., an insulin pump). Integrated diabetes management systems may be closed-loop, open-loop, or a hybrid thereof. Closed-loop systems are in full control of analyte measurement times and supplement/medication dosages and times. Open-loop systems allow a subject to be in full control of analyte measurement times and supplement/medication dosages and times. Hybrid systems can rely primarily on a closed-loop system methodology but allows a subject to intervene.

In vitro analyte monitoring systems contact a bodily fluid outside of the body. In some instances, in vitro analyte monitoring systems include a meter device that has a port for receiving the bodily fluid of the subject (e.g., on an analyte test strip/swab or via collection of the bodily fluid), which can be analyzed to determine the subject's analyte level.

Example Embodiments

A first nonlimiting example embodiment of the present disclosure is a method comprising: determining at least one physiological parameter for a subject selected from the group consisting of: a red blood cell glycation rate constant $(k_{gly})$, a red blood cell generation rate constant $(k_{gen})$, a red blood cell elimination constant $(k_{age})$, and an apparent glycation constant $(K)$, based on (1) a plurality of first glucose levels and (2) a laboratory HbA1c level (e.g., one or more laboratory HbA1c levels) using a model that considers cross-membrane glucose transport and glycation; receiving (and/or measuring) a plurality of second glucose levels for the subject over a time period; and deriving a calculated HbA1c (cHbA1c) level (e.g., using Equation 9) for the subject based on the at least one physiological parameter and the plurality of second glucose levels. The first nonlimiting example embodiment may further include one or more of: Element 1: the method further comprising: diagnosing, treating, and/or monitoring the subject based on the cHbA1c level; Element 2: Element 1 and wherein treating the subject occurs and comprises administering and/or adjusting: an insulin dosage, a glycation medication dosage, an exercise regime, a meal intake, or a combination thereof; Element 3: the method further comprising: displaying the cHbA1c level (e.g., on a system 310, a system 410, a glucose measurement device and/or closed-loop insulin pump system from which the plurality of first and/or second glucose levels were measured, or the like); Element 4: the method further comprising: calculating an adjusted HbA1c (aHbA1c) level for the subject based on the cHbA1c level, the $k_{age}$, and a defined reference $k_{age}$ $(k^{ref}_{age})$ (e.g., using Equation 10); Element 5: the method further comprising: calculating an adjusted HbA1c (aHbA1c) level for the subject based on the cHbA1c level, the $K$, and a defined reference $K$ $(K^{ref})$ (e.g., using Equation 11); Element 6: Element 5 or Element 6 and the method further comprising: diagnosing, treating, and/or monitoring the subject based on the aHbA1c level; Element 7: Element 6 and wherein treating the subject occurs and comprises administering and/or adjusting: an insulin dosage, a glycation medication dosage, an exercise regime, a meal intake, or a combination thereof; Element 8: Element 5 or Element 6 and the method further comprising: displaying the cHbA1c level and/or the aHbA1c level (e.g., on a system 310, a system 410, a glucose measurement device and/or closed-loop insulin pump system from which the plurality of first and/or second glucose levels were measured, or the like); Element 9: Element 5 or Element 6 and the method further comprising: deriving a personalized-target glucose range (e.g., using Equations 13 and 15), a personalized glucose upper limit (e.g., using Equation 15), and/or a personalized glucose lower limit (e.g., using Equation 13), based on the aHbA1c level and the laboratory HbA1c level; Element 10: Element 9 and the method further comprising: diagnosing, treating, and/or monitoring the subject based on the personalized-target glucose range, the personalized glucose upper limit, and/or the personalized glucose lower limit; Element 11: Element 10 and wherein treating the subject occurs and comprises administering and/or adjusting: an insulin dosage, a glycation medication dosage, an exercise regime, a meal intake, or a combination thereof; Element 12: Element 9 and the method further comprising: displaying the personalized-target glucose range, the personalized glucose upper limit, and/or the personalized glucose lower limit (e.g., on a system 310, a system 410, a glucose measurement device and/or closed-loop insulin pump system from which the plurality of first and/or second glucose levels were measured, or the like); Element 13: Element 9 and the method further comprising: receiving a glucose level for the subject after deriving the personalized-target glucose range, the personalized glucose upper limit, and/or the personalized glucose lower limit; and displaying (visually, audibly, and/or haptically (relating to touch)) an alarm when the glucose level is outside the personalized-target glucose range, above the personalized glucose upper limit, and/or below the personalized glucose lower limit; Element 14: Element 5 or Element 6 and the method further comprising: deriving a personalized-target average glucose (e.g., using Equation 18 or 19 or 20); Element 15: Element 14 and the method further comprising: diagnosing, treating, and/or monitoring the subject based on the personalized-target average glucose; Element 16: Element 15 and wherein treating the subject occurs and comprises administering and/or adjusting: an insulin dosage, a glycation medication dosage, an exercise regime, a meal intake, or a combination thereof; Element 17: Element 14 and the method further comprising: displaying the personalized-target average glucose (e.g., on a system 310, a system 410, a glucose measurement device and/or closed-loop insulin pump system from which the plurality of first and/or second glucose levels were measured, or the like); Element 18: Element 5 or Element 6 and the method further comprising one or more of the following based, at least in part, on the aHbA1c level: deriving a personalized treatment for subject triage; deriving a personalized treatment for titration of diabetes medication; deriving a personalized closed-loop or hybrid-closed loop control system; deriving a personalized treatment using glycation medications; identifying abnormal or diseased physiological conditions; identifying supplements and/or medicines present during testing; and identifying a physiological age; Element 19: the method further comprising one or more of the following based, at least in part, on the cHbA1c level: deriving a personalized treatment for subject triage; deriving a personalized treatment for titration of diabetes medication; deriving a personalized closed-loop or hybrid-closed loop control system; deriving a personalized treatment using glycation medications; identifying abnormal or diseased physiological conditions; identifying supplements and/or medicines present during testing; and identifying a physiological age; Element 20: the method further comprising: deriving a personalized-target glucose range (e.g., using Equations 12 and 14), a personalized glucose upper limit (e.g., using Equation 14), and/or a personalized glucose lower limit (e.g., using Equation 12) based on the $k_{gly}$ and a defined reference $k_{gly}$ $(k^{ref}_{gly})$; Element 21: Element 20 and the method further comprising: diagnosing, treating, and/or monitoring the subject based on the personalized-target glucose range, the personalized glucose upper limit, and/or the personalized glucose lower limit; Element 22: Element 21 and wherein treating the subject occurs and comprises administering and/or adjusting: an insulin dosage, a glycation medication dosage, an exercise regime, a meal intake, or a combination thereof; Element 23: Element 20 and the method further comprising: displaying the personalized-target glucose range, the personalized glucose upper limit, and/or the personalized glucose lower limit (e.g., on a system 310, a system 410, a glucose measurement device and/or closed-loop insulin pump system from which the plurality of first and/or second glucose levels were measured, or the like); and Element 24: Element 20 and the method further comprising: receiving a glucose level for the subject after deriving the personalized-target glucose range, the personalized glucose upper limit, and/or the personalized glucose lower limit; displaying (visually, audibly, and/or haptically (relating to touch)) an alarm when the glucose level is outside the personalized-target glucose range, above the personalized glucose upper limit, and/or below the personalized glucose lower limit; Element 25: the method further comprising: deriving a personalized glucose level (e.g., using Equation 16 or Equation 17) based on the $k_{gly}$, a defined reference $k_{gly}$ ($k^{ref}_{gly}$), and a measured glucose level; Element 26: Element 25 and the method further comprising: diagnosing, treating, and/or monitoring the subject based on the personalized glucose level (e.g., the personalized glucose level relative to a currently accepted glucose range or an intracellular glucose level relative to a currently accepted intracellular glucose level range (i.e., LIGL-UIGL)); Element 27: Element 26 and wherein treating the subject occurs and comprises administering and/or adjusting: an insulin dosage, a glycation medication dosage, an exercise regime, a meal intake, or a combination thereof; Element 28: Element 25 and the method further comprising: displaying the personalized glucose level (e.g., on a system 310, a system 410, a glucose measurement device and/or closed-loop insulin pump system from which the plurality of first and/or second glucose levels were measured, or the like); and Element 29: Element 25 and the method further comprising: displaying (visually, audibly, and/or haptically (relating to touch)) an alarm when the personalized glucose level is outside currently accepted respective glucose range.

A second nonlimiting example embodiment of the present disclosure is a method comprising: receiving (and/or measuring) a plurality of first glucose levels for a subject over a first time period; receiving (and/or measuring) a first glycated hemoglobin (HbA1c) level for the subject corresponding to an end of the first time period; determining at least one physiological parameter for the subject selected from the group consisting of: a red blood cell glycation rate constant ($k_{gly}$), a red blood cell generation rate constant ($k_{gen}$), a red blood cell elimination constant ($k_{age}$), and an apparent glycation constant (K), based on (1) the plurality of first glucose levels and (2) the first HbA1c level using a model that considers cross-membrane glucose transport and glycation; receiving (and/or measuring) a plurality of second glucose levels for the subject over a second time period; and deriving a calculated HbA1c (cHbA1c) level (e.g., using Equation 9) based on the at least one physiological parameter and the plurality of second glucose levels. Measuring glucose levels may involve sampling a bodily fluid from the subject using an analyte sensor; and measuring the plurality of first glucose levels with the analyte sensor. The second nonlimiting example embodiment may further include one or more of Elements 1-29.

A third nonlimiting example embodiment of the present disclosure is an analyte sensor configured to measure a glucose level in a bodily fluid; and a monitoring device comprising: one or more processors; and a memory operatively coupled to the one or more processors storing instructions which, when executed by the one or more processors, causes the one or more processors to perform the method of first or second nonlimiting example embodiment optionally including one or more of Elements 1-29.

A fourth nonlimiting example embodiment of the present disclosure is closed-loop insulin pump systems comprising:

an analyte sensor configured to measure a glucose level in a bodily fluid; an insulin pump; and a monitoring device comprising: one or more processors; and a memory operatively coupled to the one or more processors storing instructions which, when executed by the one or more processors, causes the one or more processors to perform the method of first or second nonlimiting example embodiment (optionally including one or more of Elements 1-29), where, when treatment is administered, said treatment includes administering via the closed-loop insulin pump systems an insulin dosage.

A fifth nonlimiting example embodiment is a method comprising: receiving (and/or measuring) a laboratory HbA1c level (e.g., one or more laboratory HbA1c levels) for a subject; determining a red blood cell turnover rate ($k_{age}$) for the subject (e.g., using a model that considers cross-membrane glucose transport and glycation); and calculating an adjusted HbA1c (aHbA1c) level for the subject based on the HbA1c level, the $k_{age}$, and a defined reference $k_{age}$ ($k^{ref}_{age}$) (e.g., using Equation 10). Further embodiments may further include one or more of: Element 30: the method further comprising: diagnosing, treating, and/or monitoring the subject based on the aHbA1c level; Element 31: Element 30 and wherein treating the subject occurs and comprises administering and/or adjusting: an insulin dosage, a glycation medication dosage, an exercise regime, a meal intake, or a combination thereof; Element 32: the method further comprising: displaying the aHbA1c level (e.g., on a system 310, a system 410, a glucose measurement device and/or closed-loop insulin pump system from which the plurality of first and/or second glucose levels were measured, or the like); Element 33: the method further comprising: deriving a personalized-target glucose range (e.g., using Equations 13 and 15), a personalized glucose upper limit (e.g., using Equation 15), and/or a personalized glucose lower limit (e.g., using Equation 13), based on the aHbA1c level and the laboratory HbA1c; Element 34: Element 33 and the method further comprising: diagnosing, treating, and/or monitoring the subject based on the personalized-target glucose range, the personalized glucose upper limit, and/or the personalized glucose lower limit; Element 35: Element 34 and wherein treating the subject occurs and comprises administering and/or adjusting: an insulin dosage, a glycation medication dosage, an exercise regime, a meal intake, or a combination thereof; Element 36: Element 33 and the method further comprising: displaying the personalized-target glucose range, the personalized glucose upper limit, and/or the personalized glucose lower limit (e.g., on a system 310, a system 410, a glucose measurement device and/or closed-loop insulin pump system from which the plurality of first and/or second glucose levels were measured, or the like); Element 37: Element 36 and the method further comprising: receiving a glucose level for the subject after deriving the personalized-target glucose range, the personalized glucose upper limit, and/or the personalized glucose lower limit; and displaying (visually, audibly, and/or haptically (relating to touch)) an alarm when the glucose level is outside the personalized-target glucose range, above the personalized glucose upper limit, and/or below the personalized glucose lower limit; Element 38: the method further comprising: deriving a personalized-target average glucose (e.g., using Equation 18 or 19 or 20); Element 39: Element 38 and the method further comprising: diagnosing, treating, and/or monitoring the subject based on the personalized-target average glucose; Element 40: Element 39 and wherein treating the subject occurs and comprises administering and/or adjusting: an insulin dosage, a glycation medication dosage, an exercise regime, a meal intake, or a combination thereof; Element 41: Element 38 and the method further comprising: displaying the personalized-target average glucose (e.g., on a system 310, a system 410, a glucose measurement device and/or closed-loop insulin pump system from which the plurality of first and/or second glucose levels were measured, or the like); Element 42: the method further comprising one or more of the following based, at least in part, on the aHbA1c level: deriving a personalized treatment for subject triage; deriving a personalized treatment for titration of diabetes medication; deriving a personalized closed-loop or hybrid-closed loop control system; deriving a personalized treatment using glycation medications; identifying abnormal or diseased physiological conditions; identifying supplements and/or medicines present during testing; and identifying a physiological age; Element 43: the method further comprising: deriving a personalized glucose level (e.g., using Equation 16 or Equation 17) based on the $k_{gly}$, a defined reference $k_{gly}$ ($k^{ref}_{gly}$), and a measured glucose level; Element 44: Element 43 and the method further comprising: diagnosing, treating, and/or monitoring the subject based on the personalized glucose level (e.g., the personalized glucose level relative to a currently accepted glucose range or an intracellular glucose level relative to a currently accepted intracellular glucose level range (i.e., LIGL-UIGL)); Element 45: Element 44 and wherein treating the subject occurs and comprises administering and/or adjusting: an insulin dosage, a glycation medication dosage, an exercise regime, a meal intake, or a combination thereof; Element 46: Element 43 and the method further comprising: displaying the personalized glucose level (e.g., on a system 310, a system 410, a glucose measurement device and/or closed-loop insulin pump system from which the plurality of first and/or second glucose levels were measured, or the like); and Element 47: Element 43 and the method further comprising: displaying (visually, audibly, and/or haptically (relating to touch)) an alarm when the personalized glucose level is outside currently accepted respective glucose range.

A sixth nonlimiting example embodiment is a method comprising: receiving (and/or measuring) a laboratory HbA1c level (e.g., one or more laboratory HbA1c levels) for a subject; determining an apparent glycation constant (K) for the subject (e.g., using a model that considers cross-membrane glucose transport and glycation); and calculating an adjusted HbA1c (aHbA1c) level for the subject based on the HbA1c level, the K, and a defined reference K ($K^{ref}$) (e.g., using Equation 11). The sixth nonlimiting example embodiment may further include one or more of Elements 30-47.

A seventh nonlimiting example embodiment is a method comprising: receiving (and/or measuring) a plurality of first glucose levels for a subject over a first time period; receiving (and/or measuring) a first glycated hemoglobin (HbA1c) level for the subject corresponding to an end of the first time period; determining at least one physiological parameter for the subject selected from the group consisting of: a red blood cell glycation rate constant ($k_{gly}$), a red blood cell generation rate constant ($k_{gen}$), a red blood cell elimination constant ($k_{age}$), and an apparent glycation constant (K), based on (1) the plurality of first glucose levels and (2) the first HbA1c level using a model that considers cross-membrane glucose transport and glycation; and calculating an adjusted HbA1c (aHbA1c) level for the subject based on the HbA1c level, the $k_{age}$, and a defined reference $k_{age}$ ($k^{ref}_{age}$) (e.g., using Equation 10). Measuring glucose levels may involve sampling a bodily fluid from the subject using an analyte sensor; and measuring the plurality of first glucose levels with the analyte sensor. The second nonlimiting example embodiment may further include one or more of Elements 30-47.

A eighth nonlimiting example embodiment is a method comprising: receiving (and/or measuring) a plurality of first glucose levels for a subject over a first time period; receiving (and/or measuring) a first glycated hemoglobin (HbA1c) level for the subject corresponding to an end of the first time period; determining at least one physiological parameter for the subject selected from the group consisting of: a red blood cell glycation rate constant ($k_{gly}$), a red blood cell generation rate constant ($k_{gen}$), a red blood cell elimination constant ($k_{age}$), and an apparent glycation constant (K), based on (1) the plurality of first glucose levels and (2) the first HbA1c level using a model that considers cross-membrane glucose transport and glycation; and calculating an adjusted HbA1c (aHbA1c) level for the subject based on the HbA1c level, the K, and a defined reference K ($K^{ref}$) (e.g., using Equation 11). Measuring glucose levels may involve sampling a bodily fluid from the subject using an analyte sensor; and measuring the plurality of first glucose levels with the analyte sensor. The second nonlimiting example embodiment may further include one or more of Elements 30-47.

A ninth nonlimiting example embodiment of the present disclosure is an analyte sensor configured to measure a glucose level in a bodily fluid; and a monitoring device comprising: one or more processors; and a memory operatively coupled to the one or more processors storing instructions which, when executed by the one or more processors, causes the one or more processors to perform the method of the fifth or sixth or seventh or eighth nonlimiting example embodiment (optionally including include one or more of Elements 30-47).

A tenth nonlimiting example embodiment of the present disclosure is a closed-loop insulin pump systems comprising: an analyte sensor configured to measure a glucose level in a bodily fluid; an insulin pump; and a monitoring device comprising: one or more processors; and a memory operatively coupled to the one or more processors storing instructions which, when executed by the one or more processors, causes the one or more processors to perform the method of the fifth or sixth or seventh or eighth nonlimiting example embodiment (optionally including include one or more of Elements 30-47), where, when treatment is administered, said treatment includes administering via the closed-loop insulin pump systems an insulin dosage.

An eleventh nonlimiting example embodiment of the present disclosure is a method comprising: determining at least one physiological parameter for a subject selected from the group consisting of: a red blood cell glycation rate constant ($k_{gly}$), a red blood cell generation rate constant ($k_{gen}$), a red blood cell elimination constant ($k_{age}$), and an apparent glycation constant (K), based on (1) a plurality of first glucose levels and (2) a laboratory HbA1c level (e.g., one or more laboratory HbA1c levels) using a model that considers cross-membrane glucose transport and glycation; receiving (and/or measuring) a plurality of second glucose levels for the subject over a time period; and deriving a personalized glucose level (e.g., using Equation 16 or Equation 17) based on the $k_{gly}$, a defined reference $k_{gly}$ ($k^{ref}_{gly}$), and a measured glucose level. The eleventh nonlimiting example embodiment may further include one or more of: Element 50: and the method further comprising: diagnosing, treating, and/or monitoring the subject based on the personalized glucose level (e.g., the personalized glucose level relative to a currently accepted glucose range or an intracellular glucose level relative to a currently accepted intracellular glucose level range (i.e., LIGL-UIGL)); Element 51:

Element 50 and wherein treating the subject occurs and comprises administering and/or adjusting: an insulin dosage, a glycation medication dosage, an exercise regime, a meal intake, or a combination thereof; Element 52: the method further comprising: displaying the personalized glucose level (e.g., on a system 310, a system 410, a glucose measurement device and/or closed-loop insulin pump system from which the plurality of first and/or second glucose levels were measured, or the like); and Element 53: the method further comprising: displaying (visually, audibly, and/or haptically (relating to touch)) an alarm when the personalized glucose level is outside currently accepted respective glucose range A twelfth nonlimiting example embodiment of the present disclosure is a method comprising: receiving (and/or measuring) a plurality of first glucose levels for a subject over a first time period; receiving (and/or measuring) a first glycated hemoglobin (HbA1c) level for the subject corresponding to an end of the first time period; determining at least one physiological parameter for the subject selected from the group consisting of: a red blood cell glycation rate constant ($k_{gly}$), a red blood cell generation rate constant ($k_{gen}$), a red blood cell elimination constant ($k_{age}$), and an apparent glycation constant (K), based on (1) the plurality of first glucose levels and (2) the first HbA1c level using a model that considers cross-membrane glucose transport and glycation; receiving (and/or measuring) a measured glucose level; and deriving a personalized glucose level (e.g., using Equation 16 or Equation 17) based on the $k_{gly}$, a defined reference $k_{gly}$ ($k^{ref}_{gly}$), and the measured glucose level. Measuring glucose levels may involve sampling a bodily fluid from the subject using an analyte sensor; and measuring the plurality of first glucose levels with the analyte sensor. The second nonlimiting example embodiment may further include one or more of Elements 50-53.

A thirteenth nonlimiting example embodiment of the present disclosure is an analyte sensor configured to measure a glucose level in a bodily fluid; and a monitoring device comprising: one or more processors; and a memory operatively coupled to the one or more processors storing instructions which, when executed by the one or more processors, causes the one or more processors to perform the method of eleventh or twelfth nonlimiting example embodiment optionally including one or more of Elements 50-53.

A fourteenth nonlimiting example embodiment of the present disclosure is closed-loop insulin pump systems comprising: an analyte sensor configured to measure a glucose level in a bodily fluid; an insulin pump; and a monitoring device comprising: one or more processors; and a memory operatively coupled to the one or more processors storing instructions which, when executed by the one or more processors, causes the one or more processors to perform the method of eleventh or twelfth nonlimiting example embodiment (optionally including one or more of Elements 50-53), where, when treatment is administered, said treatment includes administering via the closed-loop insulin pump systems an insulin dosage.

Unless otherwise indicated, all numbers expressing quantities and the like in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating various features are presented herein. Not all features of a physical implementation are described or shown in this application for the sake of clarity. It is understood that in the development of a physical embodiment incorporating the embodiments of the present disclosure, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, tools and methods are described herein in terms of "comprising" various components or steps, the systems, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

To facilitate a better understanding of the embodiments of the present invention, the following examples of preferred or representative embodiments are given. In no way should the following examples be read to limit, or to define, the scope of the invention.

EXAMPLES

Figures 10, 11:
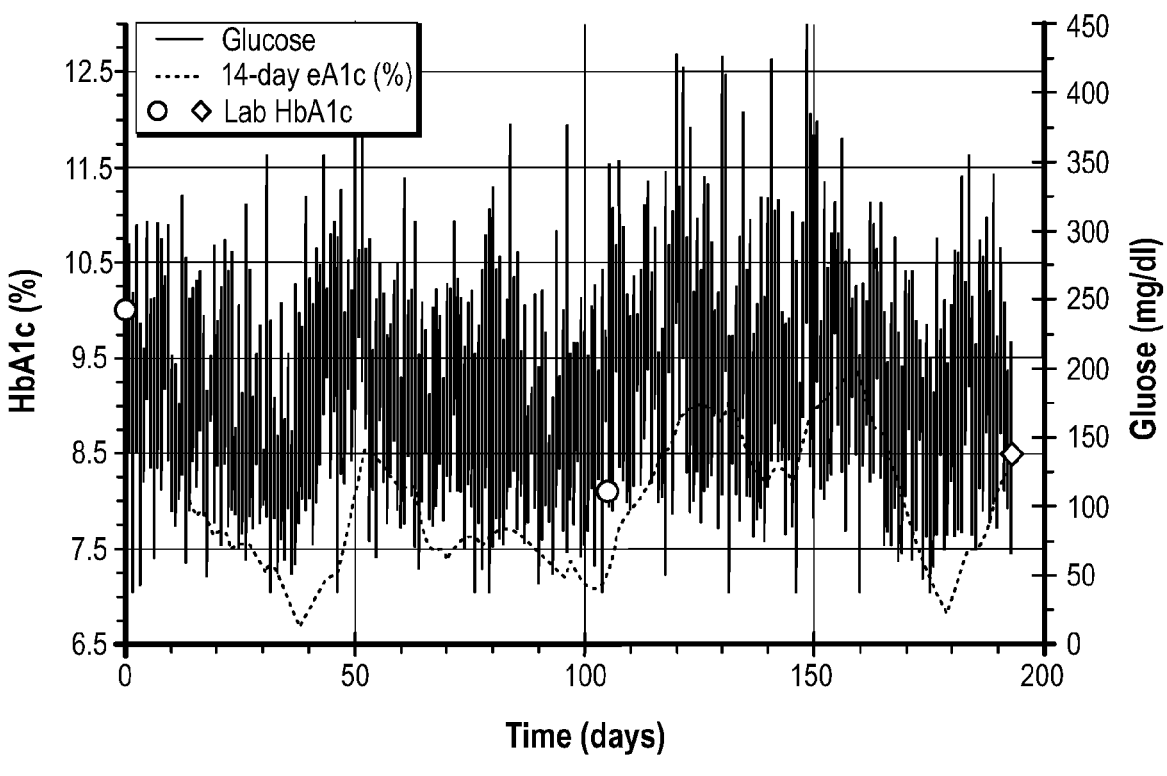
FIG. 10 is a plot of the glucose monitoring data (right y-axis) for 200 days, the three HbA1c values (left y-axis), and the estimated HbA1c values (left y-axis) based on the 14-day eHbA1c model.
FIG. 11 is the plot of FIG. 10 with a cHbA1c (left y-axis) for the first 100 days determined using $k_{gly}$ and $k_{age}$ per the methods described herein.

Example 1. The glucose monitoring data for 200 days and three HbA1c values for a single patient was used to verify the model described herein. FIG. 10 is a plot of the glucose monitoring data (right y-axis) for 200 days, the three HbA1c values (left y-axis), and the estimated HbA1c values (left y-axis) based on the 14-day eHbA1c model. As illustrated, the estimated HbA1c derived from the 14-day HbA1c model has very dramatic changes over time. However, it is unlikely that HbA1c can change this fast.

FIG. 11 is the plot of FIG. 10 with a cHbA1c (left y-axis) for the first 100 days determined using $k_{gly}$ and $k_{age}$ per the methods described herein.

Figure 12:
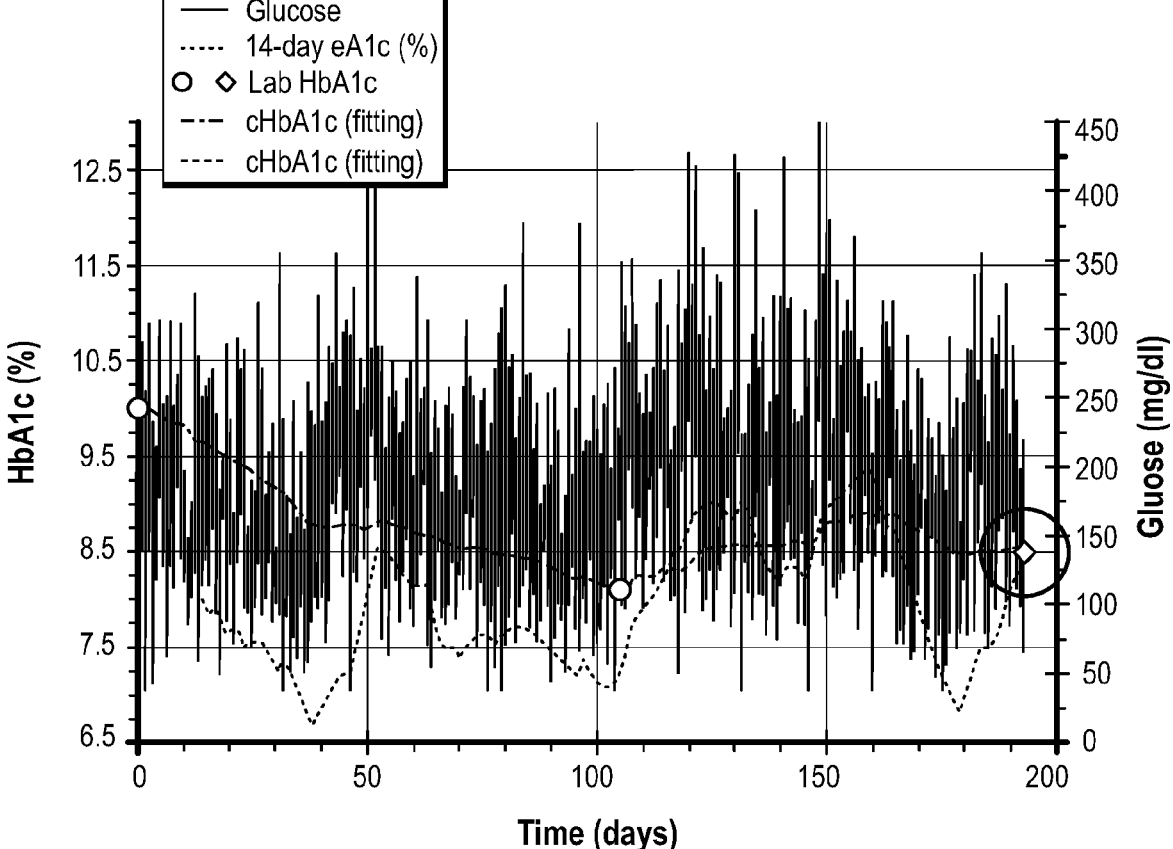
FIG. 12 is the plot of FIG. 11 with the cHbA1c (extension from day 100 to day 200, left y-axis) for the following 100 days using the $k_{gly}$ and $k_{age}$ determined relative to FIG. 10 per the methods described herein.

FIG. 12 is the plot of FIG. 11 with the cHbA1c (extension from day 100 to day 200, left y-axis) for the following 100 days using the $k_{gly}$ and $k_{age}$ determined relative to FIG. 11 per the methods described herein. The third HbA1c value was not considered in this method, but the model described herein, predicted the measured value of the third HbA1c value, which illustrates that the model described herein is in close agreement with reality.

Figure 13A:
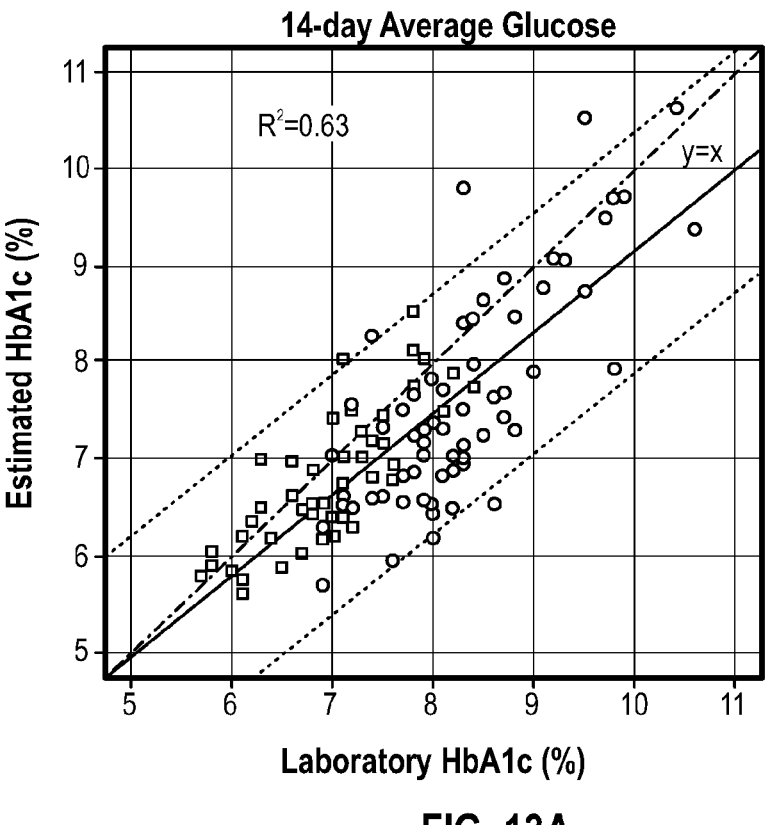
FIG. 13A is the cross-plot comparison of the estimated HbA1c level (per the 14-day glucose model) compared to laboratory HbA1c level.
Figure 13B:
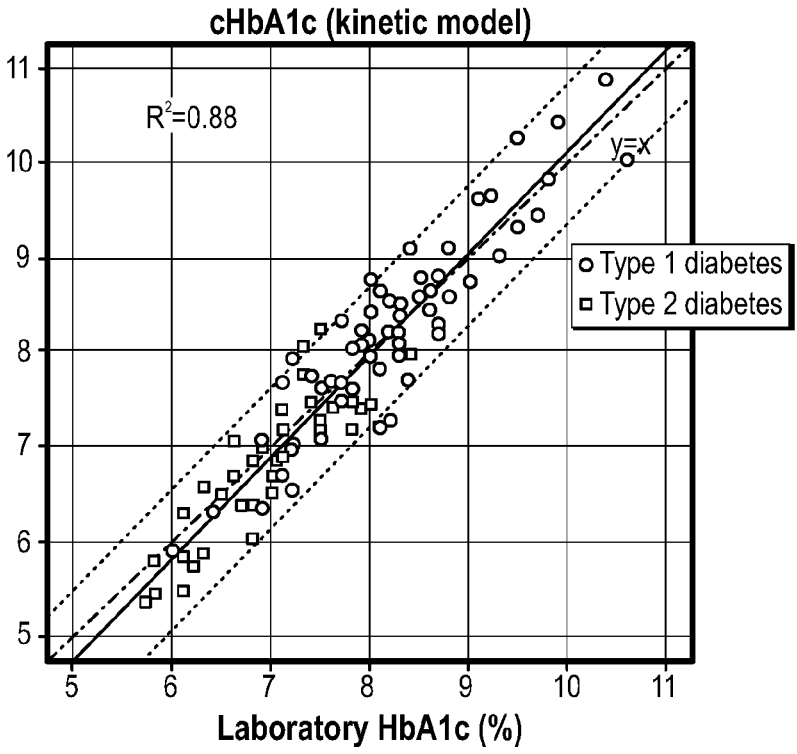
FIG. 13B is the cross-plot comparison of the cHbA1c level (per the methods described herein) compared to laboratory HbA1c level.

For a larger data set of Table 1, the same foregoing procedure was implemented as well as the 14-day glucose model to estimate HbA1c levels. FIG. 13A is the cross-plot comparison of the estimated HbA1c level (per the 14-day glucose model) compared to laboratory HbA1c level, and FIG. 13B is the cross-plot comparison of the cHbA1c level (per the methods described herein) compared to laboratory HbA1c level. The 14-day glucose model has an $R^2$ value of 0.63, while the methods described herein yield a $R^2$ of 0.88, which illustrates about a 50% reduction in variation.

TABLE 1

|  | TYPE 1 | TYPE 2 | Total |
|---|---|---|---|
| Numbers | 54 | 66 | 120 |
| Sex (M\|F) | 37\|17 | 42\|24 | 79\|41 |
| Age (year) | 42 (33-51) | 61 (54-66) | 52 (44-62) |
| Diabetes duration (years) | 20 (13-27) | 18 (11-23) | 19 (13-24) |
| Screening HbA1c (%) | 6.5 (6.4-7.1) | 8.5 (7.9-9.0) | 8.1 (7.5-9.0) |

Example 2. continuous glucose monitoring (CGM) and laboratory HbA1c data from 139 type 1 and 148 type 2 diabetes patients, enrolled onto two previous European clinical studies, were used to calculate HbA1C as detailed below. Both studies were conducted after appropriate ethical approval and participants gave written informed consent. A total of 6 months CGM data were collected using the sensor-based flash glucose monitoring system (FREE-STYLE LIBRE™; Abbott Diabetes Care, Witney, UK), while HbA1C was measured by a central laboratory (ICON Laboratories, Dublin, Ireland) at 0, 3, and 6 months of the study. Analysis was conducted with a minimum of 80% CGM coverage and no gaps in glucose data greater than 12 hrs.

RBC removal by senescence and eryptosis are complex processes and known to vary both within and across individuals. Previous work attempted to account for average RBC age variation to accurately reflect HbA1C. However, this work made no adjustment for potential differences in RBC cross-membrane glucose uptake. We have constructed a model that takes into account both RBC turnover rate and RBC cross-membrane glucose uptake by applying a recently published model (Xu Y, Dunn T C, Ajjan P A. A kinetic model for glucose levels and hemoglobin A1C provides a novel tool for individualized diabetes management. *J Diab Sci Tech.* 2020. DOI: 10.1177/1932296819897613; herein "Xu Y et al. 2020"). We used a Python/SciPy software package for all analyses and determined RBC glucose cross-membrane uptake ($k_{gly}$) and RBC turnover ($k_{age}$) as previously described in Xu Y et al. 2020. We have subsequently adapted this model for potential clinical use by constructing aHbA1C that accounts for RBC turnover rate per Formula I above.

Under the assumption of individually constant RBC life, the relationship between RBC turnover rate ($k_{age}$), RBC lifespan ($L_{RBC}$) and mean RBC age ($MA_{RBC}$) can be interconverted using the simple formula:

$$2 * MA_{RBC} = L_{RBC} = \frac{1}{k_{age}}.$$

Therefore, 1%/day standard RBC turnover rate is equivalent to 100 days of RBC life and 50 days of mean RBC age. Of note, the adjustment is not symmetric, decreasing RBC lifespan corresponds to more aHbA1C adjustment than a comparable increase in RBC lifespan.

Figure 14:
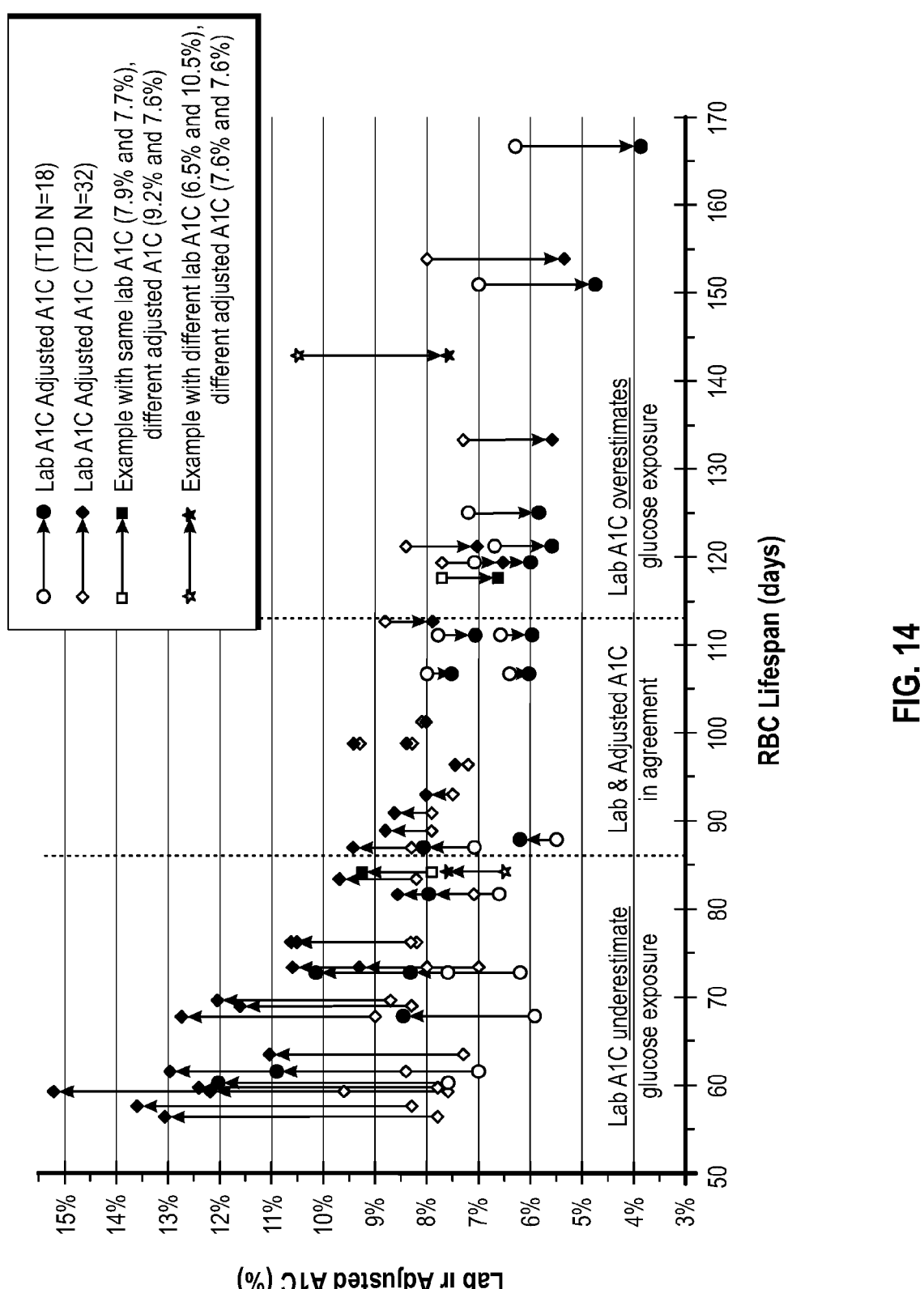
FIG. 14 is a plot of laboratory HbA1c compared to aHbA1C ("aA1C") by RBC lifespan.

FIG. 14 is a plot of laboratory HbA1c compared to aHbA1C ("aA1C") by RBC lifespan. Each individual (circles: type one diabetes, n=18; diamonds: t, n=32) is represented by 2 points, one open (laboratory HbA1c) and one solid (aHbA1C). The open squares represent similar lab A1c but different aA1c (solid squares) secondary to variable RBC lifespan. Conversely, the open stars show different laboratory HbA1c but similar aHbA1c (solid stars).

Datasets from 50 individuals met the specified criteria to calculate RBC lifespan (18 with type 1 diabetes and 32 with type 2 diabetes). Mean age of participants was 54 years (range 21-77 years), 18 of whom were females (36%). Mean RBC lifespan was 92 days, ranging from 56 to 166 days. Of the individuals studied, 68% had aHbA1C values that differed from laboratory HbA1c by more than 1.0% (11.0 mmol/mol) (FIG. 14). At an individual level, two similar laboratory HbA1c (7.7% and 7.6%, squares) showed aHbA1C of 6.5% and 10.2%, respectively (secondary to varied RBC lifespan), indicating different future risk of diabetes complications. In contrast, individuals with different laboratory HbA1c (8.8% and 6.6%, stars) demonstrated identical aHbA1C of 7.9%, placing them at similar risk of diabetes complications but potentially different risk of hypoglycemia secondary to therapy escalation likely in the patient with laboratory HbA1c of 8.8%. Generally, in individuals with RBC lifespan of 86-113 days, adjusted and laboratory HbA1c showed relatively small differences (<1.0% when laboratory HbA1c<8%). However, in those with RBC lifespan of <83 days, aHbA1C was higher than laboratory HbA1c by a median of 2.6% indicating that these individuals may be undertreated and hence at increased risk of sustained hyperglycemia and diabetes complications. Conversely, individuals with RBC lifespan>113 days had lower aHbA1C than laboratory values by a median of 1.4% and therefore some of these patients are at risk of overtreatment and precipitation of hypoglycemia (FIG. 14).

Variation in RBC lifespan and cross-membrane glucose uptake between individuals can lead to different laboratory HbA1c despite similar hyperglycemic exposure of the organs affected by diabetes complications. In order to individualize care and assess the personal risk of hyperglycemic complications, laboratory HbA1c levels should be adjusted to account for variability in RBC turnover through our proposed aHbA1C. Without this adjustment, there is a risk of overestimating glucose levels that may cause hypoglycemia through the unnecessary escalation of diabetes therapies, or alternatively, underestimation that may lead to undertreatment and subsequent higher risk of complications. In addition, there are implications for the diagnosis of prediabetes and diabetes, as there may be misclassifications if the diagnosis is based solely on laboratory HbA1c levels due to variable RBC lifespan across individuals.

In conclusion, quantitative aHbA1C, derived from laboratory HbA1c and CGM readings, has the potential to more accurately assess intracellular glycemic exposure, providing a safer and more effective glycemic guide for the management of individuals with diabetes. In this study, we chose a standard RBC lifespan of 100 days to adjust laboratory HbA1c, but further work is required to refine this and establish the best measure. Clinical studies with larger number of individuals are required to further test the accuracy of the model and correlate aHbA1C with diabetes complications and hypoglycemic exposure.

Example 3. Continuous glucose monitoring (CGM) and laboratory HbA1c data from 139 type 1 and 148 type 2 diabetes patients, enrolled onto two previous European clinical studies [10, 11], were evaluated to calculate aHbA1c as detailed below. Both studies were conducted after appropriate ethical approval and participants gave written informed consent. A total of 6 months CGM data were collected using the sensor-based flash glucose monitoring system (FreeStyle Libre™; Abbott Diabetes Care, Witney, UK), while HbA1c was measured by a central laboratory (ICON Laboratories, Dublin, Ireland) at 0, 3, and 6 months of the study. For T1D participants, the mean age was 44 years (range 18-70 years), 17 (33%) of whom were females. For T2D, the mean age was 59 years (range 33-77 years), 28 (35%) of whom were females.

In order to support quality estimates the parameters of the kinetic model, the analysis required a minimum of 70% CGM coverage and no gaps in glucose data greater than 48 hours. Each had at least one data section consisting of two HbA1c measurements connected by CGM data. Further, the parameters were successfully estimated for those individuals with sufficient day-to-day glucose variability, as evidenced by the model fit of RBC life converging between 50 and 180 days.

RBC removal by senescence and erythrocyte apoptosis are complex processes and known to vary both within and across individuals. Previous work attempted to account for average RBC age variation to accurately reflect HbA1c. However, this work made no adjustment for potential differences in RBC cross-membrane glucose uptake. We have constructed a model that takes into account both RBC turnover rate and RBC cross-membrane glucose uptake by applying our recently published model. We used Python/ SciPy software package for all analyses and determined RBC glucose cross-membrane uptake ($k_{gly}$) and RBC turnover ($k_{age}$) as previously described [9]. We have subsequently adapted this model for potential clinical use by constructing aHbA1c that accounts for RBC turnover rate, as Eq. 1 above, where HbA1c (%) is laboratory HbA1c, $k_{age}$ is individual RBC turnover rate (%/day), $k^{ref}_{age}$ is standard RBC turnover rate (1%/day).

Under the assumption of individually constant RBC life, the relationship between RBC turnover rate ($k_{age}$), RBC lifespan ($L_{RBC}$) and mean RBC age ($MA_{RBC}$) can be inter-converted using the simple formula:

$$2 * MA_{RBC} = L_{RBC} = \frac{1}{k_{age}}.$$

Therefore, 1%/day standard RBC turnover rate is equivalent to 100 days of RBC life and 50 days of mean RBC age. Of note, the adjustment is not symmetric, decreasing RBC lifespan corresponds to more aHbA1c adjustment than a comparable increase in RBC lifespan.

Figure 15:
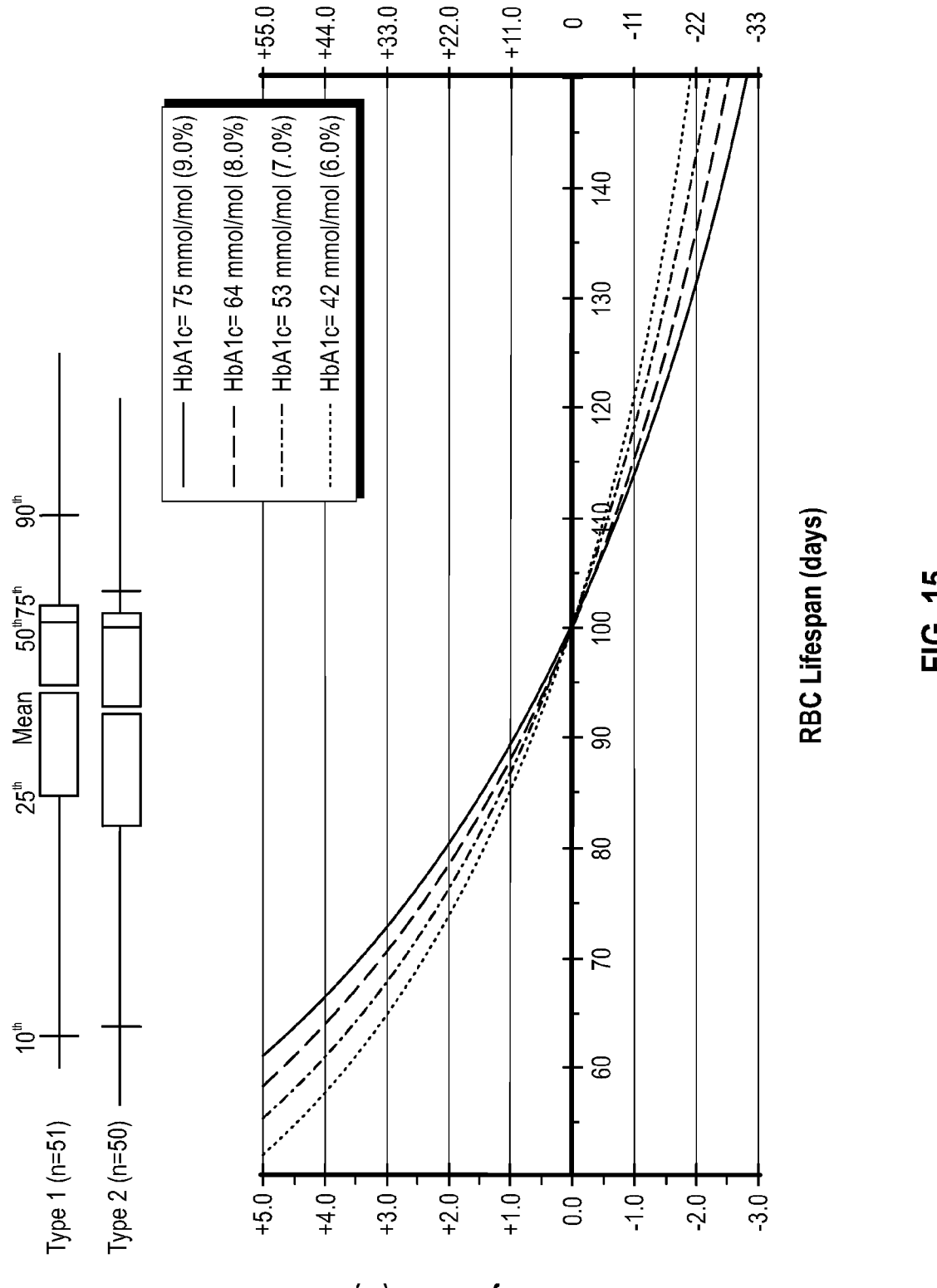
FIG. 15 is a plot that illustrates the distribution of RBC lifespan for Type 1 (n=51) and Type 2 (n=80) diabetes and adjustment to laboratory HbA1c by RBC lifespan. In this study, majority of subjects (69%) belong to the average RBC lifespan bin.

Out of 287 subjects in the original studies, 218 had sufficient CGM coverage between at least two HbA1c measurements. Of these, 131 individuals had sufficient glucose variation to have the model determine estimates for RBC lifespan and cross-membrane glucose transport rate (51 with type 1 diabetes and 80 with type 2 diabetes). Mean (median, range) RBC lifespan was 94 (100, 57-125) days in those with T1D and 92 (100, 56-151) in those with T2D (FIG. 15). In this cohort, the average differences between aHbA1c and laboratory HbA1c were 6.6 mmol/mol (0.60%) for T1D, and 9.7 mmol/mol (0.88%) for T2D subjects. The corresponding standard deviations were 17 mmol/mol (1.5%) and 19 mmol/mol (1.7%), respectively.

The put these results in a clinical context, FIG. 15 shows the adjustment to the laboratory HbA1c at different RBC lifespans. Near the borders of the interquartile range, two subjects with an identical laboratory HbA1c of 63 mmol/mol (7.9%) but different RBC lifespans of 84 and 101 days, would have RBC-lifespan-adjusted aHbA1c values of 78 mmol/mol (9.3%) and 62 mmol/mol (7.8%), respectively, indicating different future risk of diabetes complications. In contrast, individuals with different laboratory HbA1c, 60 mmol/mol (7.6%) and 75 mmol/mol (9.0%), and RBC lifespans of 84 and 101 days, would have identical aHbA1c value of 74 mmol/mol (8.9%). This would place them at similar risk of diabetes complications but potentially different risk of hypoglycemia secondary to therapy escalation likely in the patient with the higher laboratory HbA1c. Generally, in individuals with RBC lifespan of approximately 86-113 days, adjusted and laboratory HbA1c showed relatively small differences (<11 mmol/mol or 1% when laboratory HbA1c<64 mmol/mol or 8%). In this cohort, 90 (69%) subjects were within this RBC lifespan range. However, larger adjustments are possible with more extreme RBC lifespans. In those with RBC lifespan of <83 days, aHbA1c was higher than laboratory HbA1c by a median of 35 mmol/mol (3.2%) indicating that these individuals may be undertreated and hence at increased risk of sustained hyperglycaemia and diabetes complications. Conversely, individuals with RBC lifespan>113 days had lower aHbA1c than laboratory values by a median of 13 mmol/mol (1.2%) and therefore some of these patients are at risk of overtreatment and precipitation of hypoglycaemia.

Variation in RBC lifespan and cross-membrane glucose uptake between individuals can lead to different laboratory HbA1c despite similar hyperglycemic exposure of the organs affected by diabetes complications. In order to individualize care and assess the personal risk of hyperglycemic complications, laboratory HbA1c levels should be adjusted to account for variability in RBC turnover through our proposed aHbA1c. Without this adjustment, there is a risk of overestimating glucose levels that may cause hypoglycemia through the unnecessary escalation of diabetes therapies, or alternatively, underestimation that may lead to undertreatment and subsequent higher risk of complications. In addition, there are implications for the diagnosis of prediabetes and diabetes, as there may be misclassifications if the diagnosis is based solely on laboratory HbA1c levels due to variable RBC lifespan across individuals.

Several mathematical models have been developed to estimate laboratory HbA1c from glucose or TIR, emphasizing the importance of this area. A unique advantage of our model is the explicit inclusion of individual-specific RBC lifespan and glycation rate in the calculations. Therefore, the method allows estimation of RBC lifespan from CGM and HbA1c data, without the interference from glycation rate variation due to individual GLUT1 level. We presented the mathematical equation to calculate adjusted HbA1c from laboratory HbA1c and RBC lifespan. The RBC lifespan can be measured directly, which requires complicated labeling and tracing of RBCs, a process that is difficult to implement in routine clinical practice (6). In this study, we applied the previously published kinetic model (9) to estimate RBC lifespan using high quality CGM and HbA1c data.

In conclusion, quantitative aHbA1c, derived from laboratory HbA1c and CGM readings, has the potential to more accurately assess glycemic exposure of different organs, providing a safer and more effective glycemic guide for the management of individuals with diabetes. In this study, we chose a standard RBC lifespan of 100 days to adjust laboratory HbA1c, but further work is required to refine this and establish the best measure in different populations. Clinical studies with larger number of individuals are required to further test the accuracy of the model and correlate aHbA1c with diabetes complications and glycemic exposure.

Example 4. Continuous glucose monitoring (CGM) and laboratory HbA1c data from 31 type 1 diabetes patients. These individuals all had type 1 diabetes managed by a sensor-augmented pump system. The data set contained on average about 10 laboratory HbA1c values spaced by approximately 1 month for each individual, with continuous glucose monitoring throughout. A total of 304 laboratory HbA1c values were available with paired 14-day periods of CGM for analysis. The intracellular glucose (IG) was determined throughout using the Equation 17.

Figures 16A, 16B:
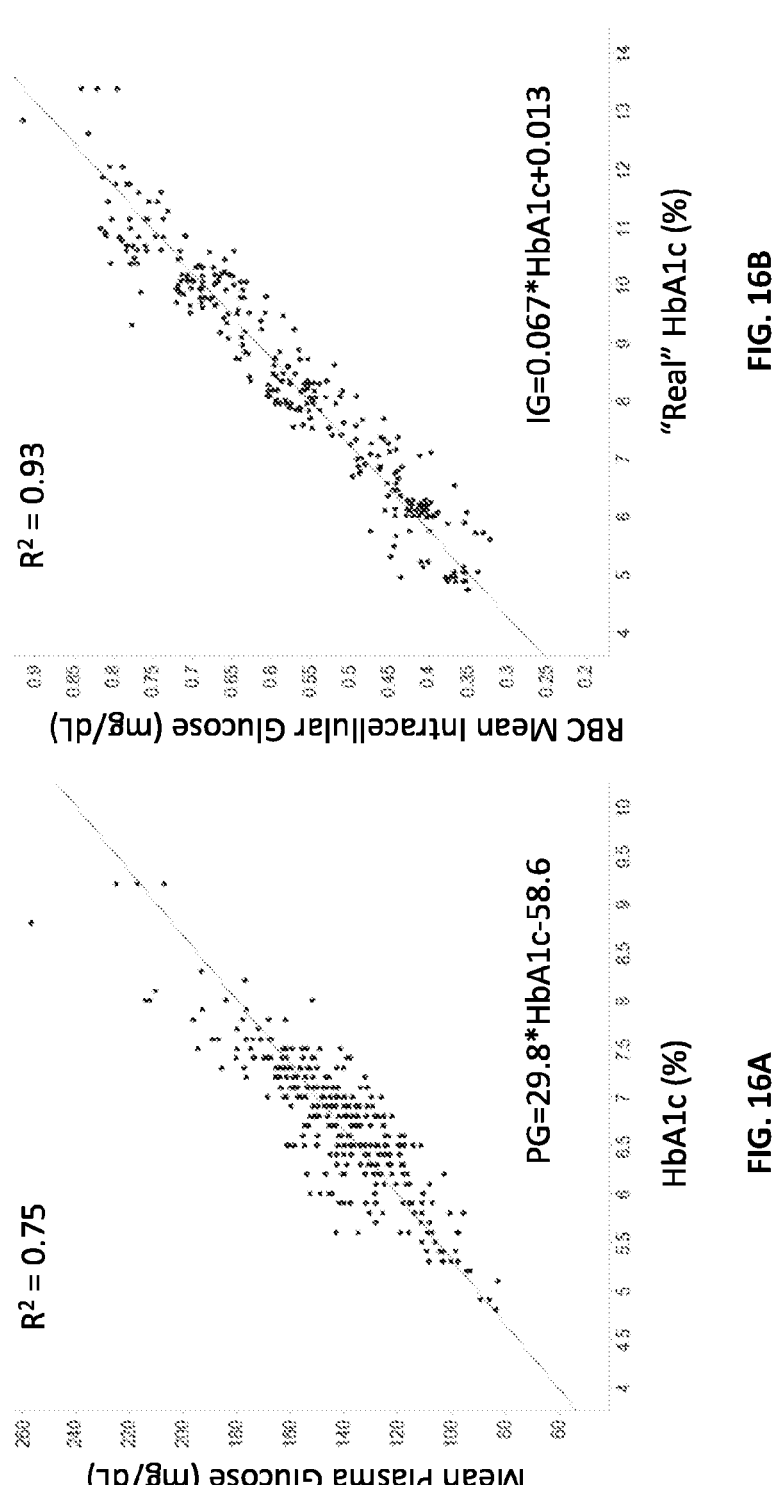
FIG. 16A is a cross-plot and correlation of the mean 14-day intracellular glucose (I)G values with the aHbA1c was prepared.
FIG. 16B is a cross-plot of the originally-collected data of 14-day mean plasma glucose (PG) and laboratory HbA1c.

FIG. 16A is a cross-plot and correlation of the mean 14-day IG values with the aHbA1c was prepared, and FIG. 16B is a cross-plot of the originally-collected data of 14-day mean plasma glucose (PG) and laboratory HbA1c. The IG method has an $R^2$ value of 0.93, while the original, unadjusted data yielded a $R^2$ of 0.75, which illustrates a significant reduction in variation.

Example 5. Continuous glucose monitoring (CGM) and laboratory HbA1c data from 31 type 1 diabetes patients. These individuals all had type 1 diabetes managed by a sensor-augmented pump system. The data set contained on average about 10 laboratory HbA1c values spaced by approximately 1 month for each individual, with continuous glucose monitoring throughout. A total of 304 laboratory HbA1c values were available with paired 14-day periods of CGM for analysis. The effective plasma glucose ($PG_{eff}$) was determined throughout using the Equation 16.

Figure 17A:
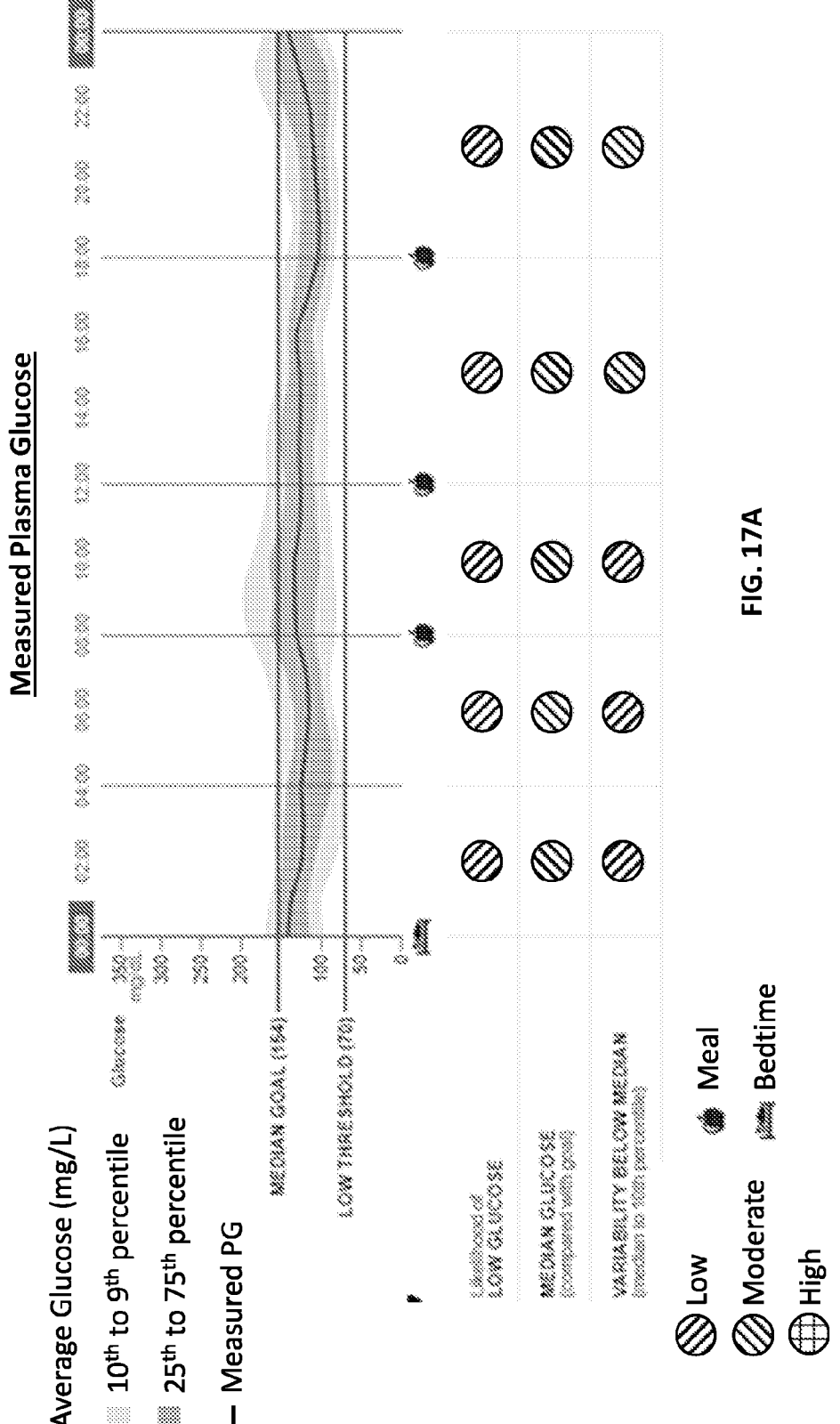
FIGS. 17A and 17B are examples of a glucose pattern insight report for the same subject using the measured PG and the $PG_{eff}$ respectively.
Figure 17B:
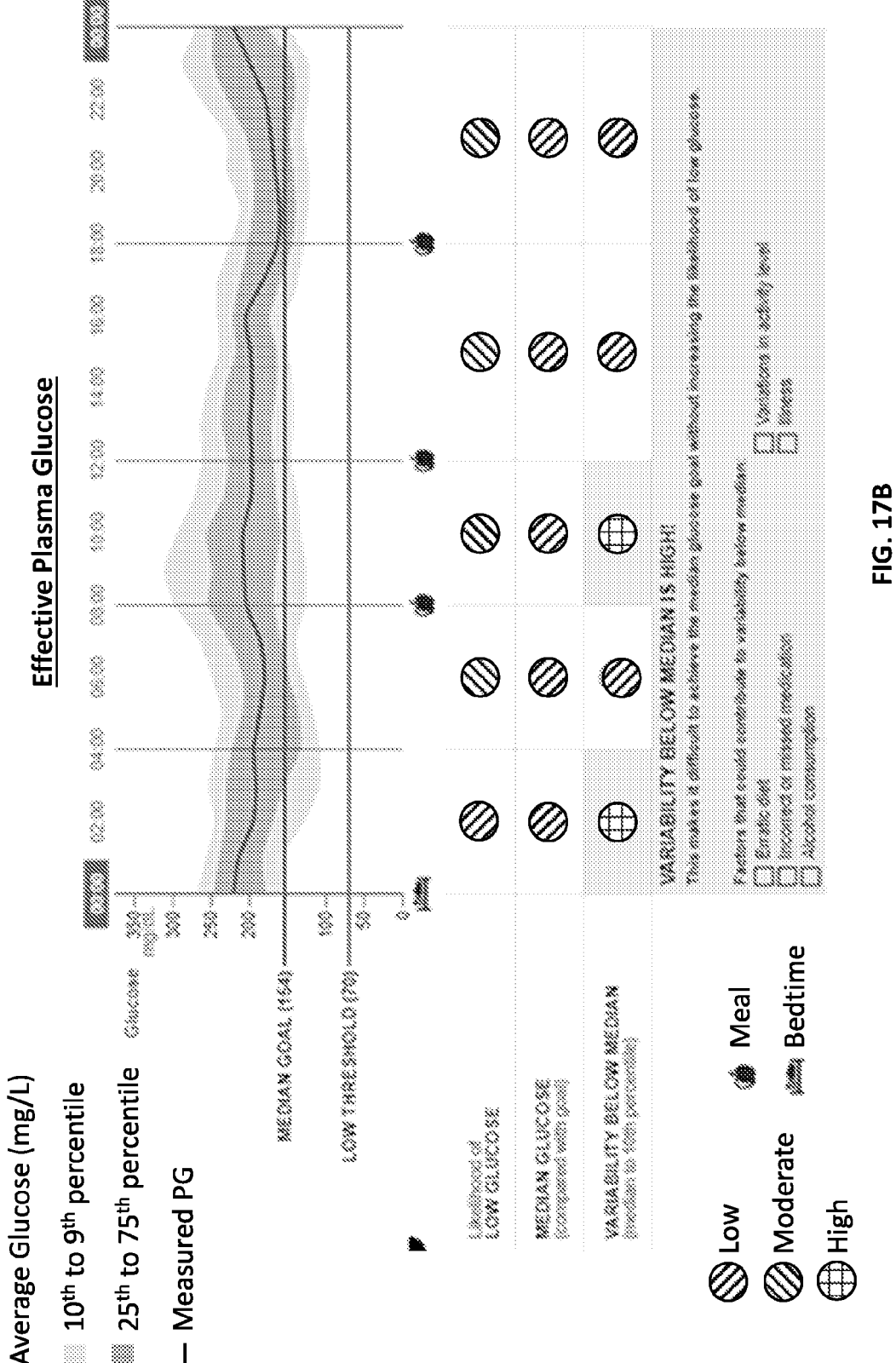

FIGS. 17A and 17B are examples of a glucose pattern insight report for the same subject (an individual with Stage 2, Mild Kidney loss) using the measured plasma glucose (PG) and the $PG_{eff}$, respectively. The $PG_{eff}$ indicates excess glucose exposure in organs and tissues, and therefore a potential source for the kidney damage. The time above target of 180 mg/dL changes from 6.7% for PG to 37.2% for $PG_{eff}$, and the time below target of 70 mg/dL decreases from 3.3% to 0.7%. These changes alter the clinical interpretation of areas of glucose control that need to be addressed to optimize short- and long-term risk reduction due to diabetes.

Therefore, the disclosed systems, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, tools and methods illustratively disclosed herein may suitably be practiced in the absence of any element that is not specifically disclosed herein and/or any optional element disclosed herein. While systems, tools and methods are described in terms of "comprising," "containing," or "including" various components or steps, the systems, tools and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

What is claimed is the following:

1. A method comprising:
   determining at least one physiological parameter for a subject selected from the group consisting of:
   a red blood cell glycation rate constant ($k_{gly}$),
   a red blood cell generation rate constant ($k_{gen}$),
   a red blood cell elimination constant ($k_{age}$), and
   an apparent glycation constant (K) based on (1) a plurality of first glucose levels and (2) a laboratory HbA1c level using a model that relies on cross-membrane glucose transport and glycation;
   measuring a plurality of second glucose levels for the subject over a time period;
   deriving a calculated HbA1c (cHbA1c) level for the subject based on the at least one physiological parameter, the laboratory HbA1c, and the plurality of second glucose levels;
   performing at least one of:
   during a data acquisition phase in which the $k_{age}$ is determined to not be available, calculating an approximate version of an adjusted HbA1c (aHbA1c) level for the subject based on the cHbA1c level, the K, and a defined reference k ($k_{ref}$); or
   after the data acquisition phase in which the $k_{age}$ is determined to be available, calculating an actual version of the aHbA1c level for the subject based on the cHbA1c level, the $k_{age}$, and a defined reference $k_{age}$ ($k^{ref}_{age}$); and
   treating the subject based on either the approximate version or the actual version of the aHbA1c level by administering and/or adjusting:
   an insulin dosage,
   a glycation medication dosage,
   an exercise regime,
   a meal intake, or
   a combination thereof.

2. The method of claim 1, wherein measuring the plurality of second glucose levels comprises:
   sampling a bodily fluid from the subject using an analyte sensor; and
   measuring the plurality of second glucose levels with the analyte sensor.

3. The method of claim 2 further comprising:
   displaying the cHbA1c level on a display of a system comprising the analyte sensor.

4. The method of claim 1, wherein measuring the plurality of second glucose levels comprises:
   sampling a bodily fluid from the subject over a time period using an analyte sensor of a closed-loop or hybrid closed-loop insulin pump system;
   measuring the plurality of second glucose levels in the bodily fluid with the analyte sensor; and
   administering, via the closed-loop or hybrid closed-loop insulin pump system, the insulin dosage based on either the approximate version or the actual version of aHbA1c.

5. The method of claim 1 further comprising: treating the subject based on either the approximate version or the actual version of the aHbA1c level by administering and/or adjusting the insulin dosage.

6. The method of claim 1 further comprising:

treating the subject based on the aHbA1c level by determining and/or administering a personalized treatment for subject triage, a personalized treatment for titration of diabetes medication, a personalized closed-loop or hybrid closed-loop control system, a personalized treatment using glycation medications, or a combination thereof.

7. A system comprising:

an analyte sensor configured to measure a glucose level in a bodily fluid;

one or more processors; and one or more hardware storage devices that store instructions that are executable by the one or more processors to cause the system to:

determine at least one physiological parameter for a subject selected from the group consisting of:

a red blood cell glycation rate constant ($k_{gly}$), a red blood cell generation rate constant ($k_{gen}$), a red blood cell elimination constant ($k_{age}$), and an apparent glycation constant (K) based on (1) a plurality of first glucose levels and (2) a laboratory HbA1c level using a model that relies on cross-membrane glucose transport and glycation;

measure a plurality of second glucose levels for the subject over a time period;

derive a calculated HbA1c (cHbA1c) level for the subject based on the at least one physiological parameter, the laboratory HbA1c, and the plurality of second glucose levels;

perform at least one of:

during a data acquisition phase in which the $k_{age}$ is determined to not be available, calculate an approximate version of an adjusted HbA1c (aHbA1c) level for the subject based on the cHbA1c level, the K, and a defined reference k ($k_{ref}$); or after the data acquisition phase in which the $k_{age}$ is determined to be available, calculating an actual version of the aHbA1c level for the subject based on the cHbA1c level, the $k_{age}$, and a defined reference $k_{age}$ ($k^{ref}_{age}$); and treat the subject based on either the approximate version or the actual version of the aHbA1c level by administering and/or adjusting:

an insulin dosage, a glycation medication dosage, an exercise regime, a meal intake, or a combination thereof.

8. The system of claim 7, wherein measuring the plurality of second glucose levels comprises:

sampling a bodily fluid from the subject using the analyte sensor; and measuring the plurality of second glucose levels with the analyte sensor.

9. The system of claim 8 wherein the instructions, when executed by the one or more processors, further causes the system to:

display the cHbA1c level on a display.

10. The system of claim 7, wherein measuring the plurality of second glucose levels comprises:

sampling a bodily fluid from the subject over a time period using the analyte sensor, which is associated with a closed-loop or hybrid-closed loop insulin pump system;

measuring the plurality of second glucose levels in the bodily fluid with the analyte sensor; and administering, via the closed-loop or hybrid closed-loop insulin pump system, the insulin dosage based on either the approximate version or the actual version of the aHbA1c.

11. The system of claim 7 wherein the instructions, when executed by the one or more processors, further causes the system to:

treat the subject based on either the approximate version or the actual version of the aHbA1c level by administering and/or adjusting the insulin dosage.

12. The system of claim 7 wherein the instructions, when executed by the one or more processors, further causes the system to:

treat the subject based on either the approximate version or the actual version of the aHbA1c level by determining and/or administering a personalized treatment for subject triage, a personalized treatment for titration of diabetes medication, a personalized closed-loop or hybrid-closed loop control system, a personalized treatment using glycation medications, or a combination thereof.

13. One or more hardware storage devices that store instructions that are executable by one or more processors to cause the one or more processors to:

determine at least one physiological parameter for a subject selected from the group consisting of:

a red blood cell glycation rate constant ($k_{gly}$), a red blood cell generation rate constant ($k_{gen}$), a red blood cell elimination constant ($k_{age}$), and an apparent glycation constant (K) based on (1) a plurality of first glucose levels and (2) a laboratory HbA1c level using a model that relies on cross-membrane glucose transport and glycation;

measure a plurality of second glucose levels for the subject over a time period;

derive a calculated HbA1c (cHbA1c) level for the subject based on the at least one physiological parameter, the laboratory HbA1c, and the plurality of second glucose levels;

perform at least one of:

during a data acquisition phase in which the $k_{age}$ is determined to not be available, calculate an approximate version of an adjusted HbA1c (aHbA1c) level for the subject based on the cHbA1c level, the K, and a defined reference k ($k_{ref}$); or after the data acquisition phase in which the $k_{age}$ is determined to be available, calculate an actual version of the aHbA1c level for the subject based on the cHbA1c level, the $k_{age}$, and a defined reference $k_{age}$ ($k^{ref}_{age}$); and treat the subject based on either the approximate version or the actual version of the aHbA1c level by administering and/or adjusting:

an insulin dosage, a glycation medication dosage, an exercise regime, a meal intake, or a combination thereof.

14. The one or more hardware storage devices of claim 13, wherein treating the subject is performed by administering and/or adjusting the insulin dosage.

* * * * *